United States Patent
Gibson et al.

(10) Patent No.: US 12,065,493 B2
(45) Date of Patent: Aug. 20, 2024

(54) ANTI-MICA/B ANTIBODIES THAT BLOCK MICA/B SHEDDING AND METHODS OF USE

(71) Applicant: Cullinan Mica Corporation, Cambridge, MA (US)

(72) Inventors: Neil Gibson, Cambridge, MA (US); Justin Chapman, Cambridge, MA (US); Xin Du, Cambridge, CA (US)

(73) Assignee: Cullinan Mica Corporation, Cambridge, MA (US)

( * ) Notice: Subject to any disclaimer, the term of this patent is extended or adjusted under 35 U.S.C. 154(b) by 693 days.

(21) Appl. No.: 17/162,585

(22) Filed: Jan. 29, 2021

(65) Prior Publication Data

US 2021/0253711 A1    Aug. 19, 2021

Related U.S. Application Data

(63) Continuation of application No. PCT/US2019/044234, filed on Jul. 30, 2019.

(60) Provisional application No. 62/712,608, filed on Jul. 31, 2018.

(51) Int. Cl.
C07K 16/28    (2006.01)

(52) U.S. Cl.
CPC ...... C07K 16/2833 (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 7,771,718 | B2 | 8/2010 | Spies et al. |
| 7,959,916 | B2 | 6/2011 | Spies et al. |
| 10,577,416 | B2 | 3/2020 | Blery et al. |
| 2008/0260727 | A1 | 10/2008 | Lanier et al. |
| 2014/0356321 | A1 | 12/2014 | Cheung et al. |
| 2015/0191542 | A1 | 7/2015 | Blery et al. |
| 2016/0030659 | A1 | 2/2016 | Cheney |
| 2016/0046689 | A1 | 2/2016 | Cheney |
| 2017/0008962 | A1 | 1/2017 | Wucherpfennig et al. |
| 2017/0121776 | A1 | 5/2017 | Soliman et al. |
| 2017/0198054 | A1 | 7/2017 | Harvey et al. |
| 2018/0154064 | A1 | 6/2018 | Cheney |
| 2019/0315870 | A1 | 10/2019 | Kuhne et al. |
| 2020/0023071 | A1 | 1/2020 | Blery et al. |
| 2020/0055939 | A1 | 2/2020 | Lombana et al. |
| 2021/0040173 | A1* | 2/2021 | Cheney .................. A61P 35/00 |

FOREIGN PATENT DOCUMENTS

| | | | |
|---|---|---|---|
| EP | 1857116 | A1 | 11/2007 |
| EP | 2970490 | A2 | 1/2016 |
| EP | 3293271 | A1 | 3/2018 |
| EP | 3529280 | A1 | 8/2019 |
| EP | 3532091 | A2 | 9/2019 |
| WO | 2013117647 | A1 | 8/2013 |
| WO | 2014/140904 | A3 | 9/2014 |
| WO | 2014140884 | A2 | 9/2014 |
| WO | 2017157895 | A1 | 9/2017 |
| WO | 2017/221072 | A2 | 12/2017 |
| WO | 2018081648 | A2 | 5/2018 |
| WO | 2018141959 | A1 | 8/2018 |
| WO | 2018201051 | A1 | 11/2018 |
| WO | 2019/147863 | A2 | 8/2019 |
| WO | 2019195409 | A1 | 10/2019 |
| WO | 2020028428 | A2 | 2/2020 |
| WO | 2020035345 | A1 | 2/2020 |

OTHER PUBLICATIONS

Culang et al. The structural basis of antibody-antigen recognition. Front. Immunol., Oct. 8, 2013. Sec. B Cell Biology. vol. 4 2013. (Year: 2013).*
Kapingidza et al. (2020). Antigen-Antibody Complexes. In: Hoeger, U., Harris, J. (eds) Vertebrate and Invertebrate Respiratory Proteins, Lipoproteins and other Body Fluid Proteins. Subcellular Biochemistry, vol. 94. Springer, Cham. https://doi.org/10.1007/978-3-030-41769-7_19 (Year: 2020).*
Canadian Intellectual Property Office, "Office Action regarding Application No. 3108022," 4 pages, dated Oct. 17, 2023.
Ferrari De Andrade, et al., "Antibody-medicated inhibition of MOCA and MICB shedding promotes NK cell-driven tumor immunity," Science, 14 pages, dated Mar. 30, 2018.
Jinushi et al., "Expression and Role of MICA and MICB in Human Hepatocellular Carcinomas and their Regulation by Retinoic Acid," Int. J. Cancer: 104, 2003, pp. 354-361.
Notification of Transmittal of the International Search Report and the Written Opinion of the International Searching Authority, or the Declaration, mailed Sep. 12, 2019, 17 pages.
Wang et al., "A Bispecific Protein rG7S-MICA Recuits Natural Killer Cells and Enhances NKG2D-Mediated Immunosurveillance Against Helatocellular Carcinoma," Cancer Letters 372 (2016) pp. 166-178.
Israel Patent Office, "Office Action," regarding Application No. 280487, 10 pages, dated Dec. 17, 2023.
Bonnafous, C., et al., "Targeting MICA with therapeutic antibodies for the treatment of cancer," Journal for Immunotherapy of Cancer, vol. I, Suppl 1, 2 pages, datedNov. 7, 2013.
Tamaki S, Sanefuzi N, Kawakami M, et al. Association between soluble MICA levels and disease stage IV oral squamous cell carcinoma in Japanese patients. Hum Immunol. 2008;69(2):88-93.
Wagner S, Wittekindt C, Reuschenbach M, et al. CD56-positive lymphocyte infiltration in relation to human papillomavirus association and prognostic significance in oropharyngeal squamous cell carcinoma. Int J Cancer. 2016;138(9):2263-2273.
Weil S, Memmer S, Lechner A, et al. Natural Killer Group 2D Ligand Depletion Reconstitutes Natural Killer Cell Immunosurveillance of Head and Neck Squamous Cell Carcinoma. Front Immunol. 2017;8:387.

(Continued)

*Primary Examiner* — Daniel E Kolker
*Assistant Examiner* — Hilary Ann Petrash
(74) *Attorney, Agent, or Firm* — McAndrews, Held & Malloy, Ltd.

(57) ABSTRACT

Provided herein are antibodies that specifically bind to MICA/B having heavy chain, light chain, variable heavy chain domains (VH), variable light chain domains (VL), and complementarity determining regions (CDRs) disclosed herein, as well as methods and uses thereof.

16 Claims, 8 Drawing Sheets

Specification includes a Sequence Listing.

(56) References Cited

OTHER PUBLICATIONS

Wulff S, Pries R, Börngen K, et al. Decreased levels of circulating regulatory NK cells in patients with head and neck cancer throughout all tumor stages. Anticancer Res. 2009;29(8):3053-3057.
Bilotta MT, Abruzzese MP, Molfetta R, et al. Activation of liver X receptor up-regulates the expression of the NKG2D ligands MICA and MICB in multiple myeloma through different molecular mechanisms. FASEB J. 2019;33(8):9489-9504.
Fionda C, Abruzzese MP, Zingoni A, et al. The IMiDs targets IKZF-1/3 and IRF4 as novel negative regulators of NK cell-activating ligands expression in multiple myeloma. Oncotarget. 2015;6(27):23609-23630.
Kosta A, Mekhloufi A, Lucantonio L, et al. GAS6/TAM signaling pathway controls MICA expression in multiple myeloma cells. Front Immunol. 2022;13:942640.
Petillo S, Capuano C, Molfetta R, et al. Immunomodulatory effect of NEDD8-activating enzyme inhibition in Multiple Myeloma: upregulation of NKG2D ligands and sensitization to Natural Killer cell recognition. Cell Death Dis. 2021;12(9):836.
Sarkar S, Germeraad WT, Rouschop KM, et al. Hypoxia induced impairment of NK cell cytotoxicity against multiple myeloma can be overcome by IL-2 activation of the NK cells. PLoS One. 2013;8(5):e64835.
Soriani A, Zingoni A, Cerboni C, et al. ATM-ATR-dependent up-regulation of DNAM-1 and NKG2D ligands on multiple myeloma cells by therapeutic agents results in enhanced NK-cell susceptibility and is associated with a senescent phenotype. Blood. 2009; 113(15):3503-3511.
Soriani A, Iannitto ML, Ricci B, et al. Reactive oxygen species-and DNA damage response-dependent NK cell activating ligand upregulation occurs at transcriptional levels and requires the transcriptional factor E2F1. J Immunol. 2014;193(2):950-960.
Swift BE, Williams BA, Kosaka Y, et al. Natural killer cell lines preferentially kill clonogenic multiple myeloma cells and decrease myeloma engraftment in a bioluminescent xenograft mouse model. Haematologica. 2012;97(7):1020-1028.
Wu X, Tao Y, Hou J, Meng X, Shi J. Valproic acid upregulates NKG2D ligand expression through an ERK-dependent mechanism and potentially enhances NK cell-mediated lysis of myeloma. Neoplasia. 2012;14(12):1178-1189.
Vulpis E, Loconte L, Peri A, et al. Impact on NK cell functions of acute versus chronic exposure to extracellular vesicle-associated MICA: Dual role in cancer immunosurveillance. J Extracell Vesicles. 2022;11(1):e12176.
Wang Y, Li H, Xu W, et al. BCMA-targeting Bispecific Antibody That Simultaneously Stimulates NKG2D-enhanced Efficacy Against Multiple Myeloma. J Immunother. 2020;43(6):175-188.
Zingoni A, Vulpis E, Cecere F, et al. MICA-129 Dimorphism and Soluble MICA Are Associated With the Progression of Multiple Myeloma. Front Immunol. 2018;9:926.
Espiau-Romera P, Courtois S, Parejo-Alonso B, Sancho P. Molecular and Metabolic Subtypes Correspondence for Pancreatic Ductal Adenocarcinoma Classification. J Clin Med. 2020;9(12):4128.
Karasinska JM, Topham JT, Kalloger SE, et al. Altered Gene Expression along the Glycolysis-Cholesterol Synthesis Axis Is Associated with Outcome in Pancreatic Cancer. Clin Cancer Res. 2020;26(1):135-146.
Li L, Shen L, Wu H, et al. An integrated analysis identifies six molecular subtypes of pancreatic ductal adenocarcinoma revealing cellular and molecular landscape. Carcinogenesis. 2023;44(10-11):726-740.
Ames E, Canter RJ, Grossenbacher SK, et al. Enhanced targeting of stem-like solid tumor cells with radiation and natural killer cells. Oncoimmunology. 2015;4(9):e1036212.
Dambrauskas Z, Svensson H, Joshi M, Hyltander A, Naredi P, IresjöBM. Expression of major histocompatibility complex class I-related chain A/B (MICA/B) in pancreatic carcinoma. Int J Oncol. 2014;44(1):99-104.
Duan X, Deng L, Chen X, et al. Clinical significance of the immunostimulatory MHC class I chain-related molecule A and NKG2D receptor on NK cells in pancreatic cancer. Med Oncol. 2011;28(2):466-474.
Gürlevik E, Fleischmann-Mundt B, Brooks J, et al. Administration of Gemcitabine After Pancreatic Tumor Resection in Mice Induces an Antitumor Immune Response Mediated by Natural Killer Cells. Gastroenterology. 2016;151(2):338-350.e7.
Miyashita T, Miki K, Kamigaki T, et al. Low-dose gemcitabine induces major histocompatibility complex class I-related chain A/B expression and enhances an antitumor innate immune response in pancreatic cancer. Clin Exp Med. 2017;17(1):19-31.
Murakami T, Homma Y, Matsuyama R, et al. Neoadjuvant chemoradiotherapy of pancreatic cancer induces a favorable immunogenic tumor microenvironment associated with increased major histocompatibility complex class I- related chain A/B expression. J Surg Oncol. 2017;116(3):416-426.
Onyeaghala G, Lane J, Pankratz N, et al. Association between MICA polymorphisms, s-MICA levels, and pancreatic cancer risk in a population-based case-control study. PLoS One. 2019;14(6):e0217868.
Peng YP, Zhu Y, Zhang JJ, et al. Comprehensive analysis of the percentage of surface receptors and cytotoxic granules positive natural killer cells in patients with pancreatic cancer, gastric cancer, and colorectal cancer. J Transl Med. 2013;11:262.
Walle T, Kraske JA, Liao B, et al. Radiotherapy orchestrates natural killer cell dependent antitumor immune responses through CXCL8. Sci Adv. 2022;8(12):eabh4050.
Xu X, Rao GS, Groh V, et al. Major histocompatibility complex class I-related chain A/B (MICA/B) expression in tumor tissue and serum of pancreatic cancer: role of uric acid accumulation in gemcitabine-induced MICA/B expression. BMC Cancer. 2011;11:194.
Raneros AB, Minguela A, Rodriguez RM, et al. Increasing TIMP3 expression by hypomethylating agents diminishes soluble MICA, MICB and ULBP2 shedding in acute myeloid leukemia, facilitating NK cell-mediated immune recognition [published correction appears in Oncotarget. Aug. 2, 20188;9(67):32881. Puras, Alfredo Minguela [corrected to Minguela, Alfredo]]. Oncotarget. 2017;8(19):31959-31976.
Rebmann V, Schütt P, Brandhorst D, et al. Soluble MICA as an independent prognostic factor for the overall survival and progression-free survival of multiple myeloma patients. Clin Immunol. 2007;123(1):114-120.
Sheppard S, Ferry A, Guedes J, Guerra N. The Paradoxical Role of NKG2D in Cancer Immunity. Front Immunol. 2018;9:1808.
Cascone R, Carlucci A, Pierdiluca M, Santini M, Fiorelli A. Prognostic value of soluble major histocompatibility complex class I polypeptide-related sequence A in non-small-cell lung cancer-significance and development. Lung Cancer (Auckl). 2017;8:161-167.
Ullrich E, Koch J, Cerwenka A, Steinle A. New prospects on the NKG2D/NKG2DL system for oncology. Oncoimmunology. 2013;2(10):e26097.
Wu JD, Atteridge CL, Wang X, Seya T, Plymate SR. Obstructing shedding of the immunostimulatory MHC class I chain-related gene B prevents tumor formation. Clin Cancer Res. 2009;15(2):632-640.
Lazarova M, Steinle A. The NKG2D axis: an emerging target in cancer immunotherapy. Expert Opin Ther Targets. 2019;23(4):281-294.
Del Toro-Arreola S, Arreygue-Garcia N, Aguilar-Lemarroy A, et al. MHC class I-related chain A and B ligands are differentially expressed in human cervical cancer cell lines. Cancer Cell Int. 2011;11:15.
Zhang J, Liu D, Li G, et al. Antibody-mediated neutralization of soluble MIC significantly enhances CTLA4 blockade therapy. Sci Adv. 2017;3(5):e1602133.
Waldhauer I, Goehlsdorf D, Gieseke F, et al. Tumor-associated MICA is shed by ADAM proteases. Cancer Res. 2008;68(15):6368-6376.
Wang WH, Cheung-Lau J, Chen Y, Lewis M, Tang QM. Specific and high-resolution identification of monoclonal antibody fragments detected by capillary electrophoresis-sodium dodecyl sulfate using reversed-phase HPLC with top-down mass spectrometry analysis. MAbs. 2019;11(7):1233-1244.

(56) References Cited

OTHER PUBLICATIONS

Wang X, Lundgren AD, Singh P, Goodlett DR, Plymate SR, Wu JD. An six-amino acid motif in the alpha3 domain of MICA is the cancer therapeutic target to inhibit shedding. Biochem Biophys Res Commun. 2009;387(3):476-481.
Weiss T, Schneider H, Silginer M, et al. NKG2D-Dependent Antitumor Effects of Chemotherapy and Radiotherapy against Glioblastoma. Clin Cancer Res. 2018;24(4):882-895.
Weiss-Steider B, Soto-Cruz I, Martinez-Campos CA, Mendoza-Rincon JF. Expression of MICA, MICB and NKG2D in human leukemic myelomonocytic and cervical cancer cells. J Exp Clin Cancer Res. 2011;30(1):37.
Wilson JM, Schuyler AJ, Schroeder N, Platts-Mills TA. Galactose-α-1,3-Galactose: Atypical Food Allergen or Model IgE Hypersensitivity?. Curr Allergy Asthma Rep. 2017;17(1):8.
Wu L, Zhang C, Zhang J. HMBOX1 negatively regulates NK cell functions by suppressing the NKG2D/DAP10 signaling pathway. Cell Mol Immunol. 2011;8(5):433-440.
Xiao L, Cen D, Gan H, et al. Adoptive Transfer of NKG2D Car mRNA-Engineered Natural Killer Cells in Colorectal Cancer Patients. Mol Ther. 2019;27(6):1114-1125.
Chen Y, Lin WS, Zhu WF, et al. Tumor MICA status predicts the efficacy of immunotherapy with cytokine-induced killer cells for patients with gastric cancer. Immunol Res. 2016; 64(1):251-259.
Du Y, Wei Y. Therapeutic Potential of Natural Killer Cells in Gastric Cancer. Front Immunol. 2019; 9:3095.
Hong JY, An JY, Lee J, et al. Claudin 18.2 expression in various tumor types and its role as a potential target in advanced gastric cancer. Transl Cancer Res. 2020;9(5):3367-3374.
Janjigian YY, Werner D, Pauligk C, et al. Prognosis of metastatic gastric and gastroesophageal junction cancer by HER2 status: a European and USA International collaborative analysis. Ann Oncol. 2012; 23(10):2656-2662.
Keshavjee SH, Moy RH, Reiner SL, et al. Gastric Cancer and the Immune System: The Key to Improving Outcomes? Cancers (Basel). 2022; 14(23):5940.
Li W, Zhang X, Du Y, et al. HER2-targeted advanced metastatic gastric/gastroesophageal junction adenocarcinoma: treatment landscape and future perspectives. Biomark Res. 2022; 10(1):71.
Liu X, Sun M, Yu S, et al. Potential therapeutic strategy for gastric cancer peritoneal metastasis by NKG2D ligands-specific T cells. Onco Targets Ther. 2015;8: 3095-3104.
Moentenich V, Gebauer F, Comut E, et al. Claudin 18.2 expression in esophageal adenocarcinoma and its potential impact on future treatment strategies. Oncol Lett. 2020; 19(6):3665-3670.
Osaki T, Saito H, Yoshikawa T, et al. Decreased NKG2D expression on CD8+ T cell is involved in immune evasion in patients with gastric cancer. Clin Cancer Res. 2007;13(2 Pt 1):382-387.
Qu J, Hou Z, Han Q, et al. Intracellular poly(I:C) initiated gastric adenocarcinoma cell apoptosis and subsequently ameliorated NK cell functions. J Interferon Cytokine Res. 2014; 34(1):52-59.
Ribeiro CH, Kramm K, Galvez-Jirón F, et al. Clinical significance of tumor expression of major histocompatibility complex class I-related chains A and B (MICA/B) in gastric cancer patients. Oncol Rep. 2016; 35(3):1309-1317.
Sahin U, Koslowski M, Dhaene K, et al. Claudin-18 splice variant 2 is a pan-cancer target suitable for therapeutic antibody development. Clin Cancer Res. 2008; 14(23):7624-7634.
Sahin U, Schuler M, Richly H, et al. A phase I dose-escalation study of IMAB362 (Zolbetuximab) in patients with advanced gastric and gastro-oesophageal junction cancer. Eur J Cancer. 2018; 100:17-26.
Sonbol MB, Pathak S, Bekaii-Saab T. The treatment landscape for gastroesophageal adenocarcinomas. Clin Adv Hematol Oncol. 2022;20(3):169-177.
Toledo-Stuardo K, Ribeiro CH, Canals A, et al. Major Histocompatibility Complex Class I-Related Chain A (Mica) Allelic Variants Associate With Susceptibility and Prognosis of Gastric Cancer. Front Immunol. 2021;12:645528.

Ungureanu BS, Lungulescu CV, Pirici D, et al. Clinicopathologic Relevance of Claudin 18.2 Expression in Gastric Cancer: A Meta-Analysis. Front Oncol. 2021;11:643872.
Zhao S, Wang H, Nie Y, et al. Midkine upregulates MICA/B expression in human gastric cancer cells and decreases natural killer cell cytotoxicity. Cancer Immunol Immunother. 2012;61(10):1745-1753.
Bisheshar SK, De Ruiter EJ, Devriese LA, Willems SM. The prognostic role of NK cells and their ligands in squamous cell carcinoma of the head and neck: a systematic review and meta-analysis. Oncoimmunology. 2020;9(1):1747345.
Charap AJ, Enokida T, Brody R, et al. Landscape of natural killer cell activity in head and neck squamous cell carcinoma. J Immunother Cancer. 2020;8(2):e001523.
Chen S, Ying M, Lin X, et al. Expression of MICA in oral squamous carcinoma cells and its effect on NK cells. Int J Clin Exp Med. 2015;8(10):18208-18212.
Dasgupta S, Bhattacharya-Chatterjee M, O'Malley BW Jr, Chatterjee SK. Inhibition of NK cell activity through TGF-beta 1 by down-regulation of NKG2D in a murine model of head and neck cancer. J Immunol. 2005;175(8):5541-5550.
Elmusrati A, Wang J, Wang CY. Tumor microenvironment and immune evasion in head and neck squamous cell carcinoma. Int J Oral Sci. 2021;13(1):24.
Friedman J, Padget M, Lee J, et al. Direct and antibody-dependent cell-mediated cytotoxicity of head and neck squamous cell carcinoma cells by high-affinity natural killer cells. Oral Oncol. 2019;90:38-44.
Klöß S, Chambron N, Gardlowski T, et al. Increased sMICA and TGFB1 levels in HNSCC patients impair NKG2D-dependent functionality of activated NK cells. Oncoimmunology. 2015;4(11):e1055993.
Klöss S, Chambron N, Gardlowski T, et al. Cetuximab Reconstitutes Pro-Inflammatory Cytokine Secretions and Tumor-Infiltrating Capabilities of sMICA-Inhibited NK Cells in HNSCC Tumor Spheroids. Front Immunol. 2015;6:543.
95. Lee, June-Chul et al. "Elevated TGF-beta1 secretion and down-modulation of NKG2D underlies impaired NK cytotoxicity in cancer patients." Journal of immunology (Baltimore, Md. :1950) vol. 172,12 (2004): 7335-40.
Lu J, Chen XM, Huang HR, et al. Detailed analysis of inflammatory cell infiltration and the prognostic impact on nasopharyngeal carcinoma. Head Neck. 2018;40(6):1245-1253.
Lu H, Dai W, Guo Z, et al. High Abundance of Intratumoral γδ T Cells Favors a Better Prognosis in Head and Neck Squamous Cell Carcinoma: A Bioinformatic Analysis. Front Immunol. 2020;11:573920.
Mandal R, Şenbabaoğlu Y, Desrichard A, et al. The head and neck cancer immune landscape and its immunotherapeutic implications. JCI Insight. 2016;1(17):e89829.
Schantz SP, Savage HE, Racz T, et al. Natural killer cells and metastases from pharyngeal carcinoma. Am J Surg. 1989;158(4):361-366.
Schantz SP, Ordonez NG. Quantitation of natural killer cell function and risk of metastatic poorly differentiated head and neck cancer. Nat Immun Cell Growth Regul. 1991;10(5):278-288.
Ames, E, Canter RJ, Grossenbacher SK, et al. NK Cells Preferentially Target Tumor Cells with a Cancer Stem Cell Phenotype. J Immunol. 2015;195(8):4010-4019.
Lazarova M, Wels WS, Steinle A. Arming cytotoxic lymphocytes for cancer immunotherapy by means of the NKG2D/NKG2D-ligand system. Expert Opin Biol Ther. 2020;20(12):1491-1501.
Ashiru O, Boutet P, Fernández-Messina L, et al. Natural killer cell cytotoxicity is suppressed by exposure to the human NKG2D ligand MICA*008 that is shed by tumor cells in exosomes. Cancer Res. 2010;70(2):481-489.
Bosques CJ, Collins BE, Meador JW 3rd, et al. Chinese hamster ovary cells can produce galactose-α-1,3-galactose antigens on proteins [published correction appears in Nat Biotechnol. May 2011;29(5):459]. Nat Biotechnol. 2010;28(11):1153-1156.
Cao W, Xi X, Hao Z, et al. RAET1E2, a soluble isoform of the UL16-binding protein RAET1E produced by tumor cells, inhibits NKG2D-mediated NK cytotoxicity. J Biol Chem. 2007;282(26):18922-18928.

(56) References Cited

OTHER PUBLICATIONS

Chen JL, Chang CC, Huang YS, et al. Persistently elevated soluble MHC class I polypeptide-related sequence A and transforming growth factor-β1 levels are poor prognostic factors in head and neck squamous cell carcinoma after definitive chemoradiotherapy. PLoS One. 2018;13(8):e0202224.

Chitadze G, Lettau M, Bhat J, et al. Shedding of endogenous MHC class I-related chain molecules A and B from different human tumor entities: heterogeneous involvement of the "a disintegrin and metalloproteases" 10 and 17. Int J Cancer. 2013;133(7):1557-1566.

Choy MK, Phipps ME. MICA polymorphism: biology and importance in immunity and disease. Trends Mol Med. 2010;16(3):97-106.

Du C, Bevers J 3rd, Cook R, et al. MICA immune complex formed with alpha 3 domain-specific antibody activates human NK cells in a Fc-dependent manner. J Immunother Cancer. 2019;7(1):207.

Fionda C, Soriani A, Malgarini G, Iannitto ML, Santoni A, Cippitelli M. Heat shock protein-90 inhibitors increase MHC class I-related chain A and B ligand expression on multiple myeloma cells and their ability to trigger NK cell degranulation. J Immunol. 2009;183(7):4385-4394.

Fionda C, Soriani A, Zingoni A, Santoni A, Cippitelli M. NKG2D and DNAM-1 Ligands: Molecular Targets for NK Cell-Mediated Immunotherapeutic Intervention in Multiple Myeloma. Biomed Res Int. 2015;2015:178698.

Friese MA, Platten M, Lutz SZ, et al. MICA/NKG2D-mediated immunogene therapy of experimental gliomas. Cancer Res. 2003;63(24):8996-9006.

De la Fuente J, Pacheco I, Villar M, Cabezas-Cruz A. The alpha-Gal syndrome: new insights into the tick-host conflict and cooperation. Parasit Vectors. 2019;12(1):154.

Groh V, Steinle A, Bauer S, Spies T. Recognition of stress-induced MHC molecules by intestinal epithelial gammadelta T cells. Science. 1998;279(5357):1737-1740.

Gavlovsky PJ, Tonnerre P, Gérard N, et al. Alternative Splice Transcripts for MHC Class I-like MICA Encode Novel NKG2D Ligands with Agonist or Antagonist Functions. J Immunol. 2016;197(3):736-746.

Lombana TN, Matsumoto ML, Berkley AM, et al. High-resolution glycosylation site-engineering method identifies MICA epitope critical for shedding inhibition activity of anti-MICA antibodies. MAbs. 2019;11(1):75-93.

Guan Y, Li W, Hou Z, et al. HBV suppresses expression of MICA/B on hepatoma cells through up-regulation of transcription factors GATA2 and GATA3 to escape from NK cell surveillance. Oncotarget. 2016;7(35):56107-56119.

Guerra N, Tan YX, Joncker NT, et al. NKG2D-deficient mice are defective in tumor surveillance in models of spontaneous malignancy [published correction appears in Immunity. May 2008;28(5):723.

Holdenrieder S, Stieber P, Peterfi A, Nagel D, Steinle A, Salih HR. Soluble MICA in malignant diseases. Int J Cancer. 2006;118(3):684-687.

Ferrari de Andrade L, Kumar S, Luoma AM, et al. Inhibition of MICA and MICB Shedding Elicits NK-Cell-Mediated Immunity against Tumors Resistant to Cytotoxic T Cells. Cancer Immunol Res. 2020;8(6):769-780.

Jinushi M, Hodi FS, Dranoff G. Therapy-induced antibodies to MHC class I chain-related protein A antagonize immune suppression and stimulate antitumor cytotoxicity. Proc Natl Acad Sci U S A. 2006; 103(24):9190-9195.

Kellner C, Lutz S, Oberg HH, et al. Tumor cell lysis and synergistically enhanced antibody-dependent cell-mediated cytotoxicity by NKG2D engagement with a bispecific immunoligand targeting the HER2 antigen. Biol Chem. 2021;403(5-6):545-556.

Kohga K, Takehara T, Tatsumi T, et al. Serum levels of soluble major histocompatibility complex (MHC) class I-related chain A in patients with chronic liver diseases and changes during transcatheter arterial embolization for hepatocellular carcinoma. Cancer Sci. 2008;99(8):1643-1649.

Kumar V, Yi Lo PH, Sawai H, et al. Soluble MICA and a MICA variation as possible prognostic biomarkers for HBV-induced hepatocellular carcinoma. PLoS One. 2012;7(9):e44743.

Lanier LL. NKG2D Receptor and Its Ligands in Host Defense. Cancer Immunol Res. 2015;3(6):575-582.

Lerner E, Woroniecka K, D'Anniballe V, et al. A Novel MHC-Independent Mechanism of Tumor Cell Killing by CD8+ T Cells. bioRxiv 2023.02.02.526713.

Li P, Morris DL, Willcox BE, Steinle A, Spies T, Strong RK. Complex structure of the activating immunoreceptor NKG2D and its MHC class I-like ligand MICA. Nat Immunol. 2001;2(5):443-451.

Lu X, Zhu A, Cai X, et al. Role of NKG2D in cytokine-induced killer cells against multiple myeloma cells. Cancer Biol Ther. 2012;13(8):623-629.

Maccalli C, Giannarelli D, Chiarucci C, et al. Soluble NKG2D ligands are biomarkers associated with the clinical outcome to immune checkpoint blockade therapy of metastatic melanoma patients. Oncoimmunology. 2017;6(7):e1323618.

Fang L, Gong J, Wang Y, et al. MICA/B expression is inhibited by unfolded protein response and associated with poor prognosis in human hepatocellular carcinoma. J Exp Clin Cancer Res. 2014;33(1):76.

Jinushi M, Vanneman M, Munshi NC, et al. MHC class I chain-related protein A antibodies and shedding are associated with the progression of multiple myeloma. Proc Natl Acad Sci U S A. 2008; 105(4):1285-1290.

Isernhagen A, Schilling D, Monecke S, et al. The MICA-129Met/Val dimorphism affects plasma membrane expression and shedding of the NKG2D ligand MICA. Immunogenetics. 2016;68(2):109-123.

Kim Y, Born C, Bléry M, Steinle A. MICAgen Mice Recapitulate the Highly Restricted but Activation-Inducible Expression of the Paradigmatic Human NKG2D Ligand MICA. Front Immunol. 2020;11:960.

Zingoni A, Cecere F, Vulpis E, et al. Genotoxic Stress Induces Senescence-Associated ADAM10-Dependent Release of NKG2D Mic Ligands in Multiple Myeloma Cells. J Immunol. 2015;195(2):736-748.

Nayyar G, Chu Y, Cairo MS. Overcoming Resistance to Natural Killer Cell Based Immunotherapies for Solid Tumors. Front Oncol. Feb. 11, 2019;9:51.

Meyer A, Carapito R, Ott L, Radosavljevic M, Georgel P, Adams EJ, Parham P, Bontrop RE, Blancher A, Bahram S. High diversity of MIC genes in non-human primates. Immunogenetics. Oct. 2014;66(9-10):581-7.

Zingoni A, Molfetta R, Fionda C, et al. NKG2D and Its Ligands: "One for All, All for One". Front Immunol. 2018;9:476.

Schmiedel D, Mandelboim O. NKG2D Ligands-Critical Targets for Cancer Immune Escape and Therapy. Front Immunol. 2018;9:2040.

Abrahao-Machado LF, Scapulatempo-Neto C. HER2 testing in gastric cancer: An update. World J Gastroenterol. 2016;22(19):4619-4625.

Barra WF, Moreira FC, Pereira Cruz AM, et al. GEJ cancers: gastric or esophageal tumors? searching for the answer according to molecular identity. Oncotarget. 2017;8(61):104286-104294.

Dhar P, Wu JD. NKG2D and its ligands in cancer. Curr Opin Immunol. Apr. 2018;51:55-61.

Liu H, Wang S, Xin J, Wang J, Yao C, Zhang Z. Role of NKG2D and its ligands in cancer immunotherapy. Am J Cancer Res. 2019;9(10):2064-2078.

Oyer JL, Gitto SB, Altomare DA, Copik AJ. PD-L1 blockade enhances anti-tumor efficacy of NK cells. Oncoimmunology. 2018;7(11):e1509819.

Li JJ, Pan K, Gu MF, et al. Prognostic value of soluble MICA levels in the serum of patients with advanced hepatocellular carcinoma. Chin J Cancer. 2013;32(3):141-148.

Salih HR, Rammensee HG, Steinle A. Cutting edge: down-regulation of MICA on human tumors by proteolytic shedding. J Immunol. 2002;169(8):4098-4102.

(56) References Cited

OTHER PUBLICATIONS

Sakiyama MJ, Espinoza I, Reddy A, et al. Race-associated expression of MHC class I polypeptide-related sequence A (MICA) in prostate cancer. Exp Mol Pathol. 2019;108:173-182.

* cited by examiner

NKG2D expression of
TIL NK cells

NKG2D expression of TIL alpha beta CD8⁺ T cells

NKG2D expression of TIL gamma delta T cells

Soluble MicA

Surface MicA

Non-competition ctrl 5C3 binds α1/α2 domain

SEQUENCE LISTING

```
<160> NUMBER OF SEQ ID NOS: 34

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Ser Lys Ser Leu Leu His Ser Asn Gly Asn Thr Tyr Leu Tyr
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Met Ser Asn Leu Ala Ser
```

```
<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Gln His Leu Glu Tyr Pro Phe Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Asn Tyr Ala Met Ser
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Ser Pro Gly Gly Asp Tyr Ile Tyr Tyr Ala Asp Thr Val Lys
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Arg His Tyr Gly Ser Tyr Ala Met Asp Tyr
1               5                   10

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45
```

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Gln Glu Ser Gly Glu Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Tyr Ile Ser Pro Gly Gly Asp Tyr Ile Tyr Tyr Ala Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Met Tyr Tyr Cys
                85                  90                  95

Thr Thr Asp Arg Arg His Tyr Gly Ser Tyr Ala Met Asp Tyr Trp Gly
            100                 105                 110

Gln Gly Ile Ser Val Thr Val Ser Ser
        115                 120

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ala Ser Ser Ser Val Ser Ser Asn Tyr Leu His
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Thr Ser Asn Leu Ala Ser
1               5

<210> SEQ ID NO 11
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Gln Phe His Arg Ser Pro Phe Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Ser Leu Thr Ala Phe Gly Val Asn
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met Ile Trp Gly Asp Gly Asn Thr Asp Tyr Asn Ser Thr Leu Arg Ser
1               5                   10                  15

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Thr Tyr Tyr Gly Asn Tyr Ala Gly Leu Gly Tyr
1               5                   10

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ile Val Leu Thr Gln Ser Pro Ala Ile Met Ser Ala Ser Ile Gly
1               5                   10                  15

Glu Arg Val Thr Met Thr Cys Thr Ala Ser Ser Ser Val Ser Ser Asn
                20                  25                  30

Tyr Leu His Trp Tyr Gln Gln Lys Pro Arg Ser Ser Pro Lys Leu Trp
            35                  40                  45

Ile Tyr Thr Thr Ser Asn Leu Ala Ser Gly Val Pro Thr Arg Phe Ser
        50                  55                  60

Gly Ser Gly Ser Gly Thr Ser Tyr Ser Leu Thr Ile Ser Ser Met Glu
65                  70                  75                  80
```

```
Ala Glu Asp Ala Ala Thr Tyr Tyr Cys His Gln Phe His Arg Ser Pro
                85                  90                  95

Phe Thr Phe Gly Ser Gly Thr Lys Leu Glu Ile Lys
            100                 105

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Phe
            20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Thr Leu Arg
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Arg Tyr Phe Cys Ala
                85                  90                  95

Arg Glu Thr Tyr Tyr Gly Asn Tyr Ala Gly Leu Gly Tyr Trp Gly Gln
            100                 105                 110

Gly Thr Leu Val Thr Val Ser Ala
        115                 120

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Ser Lys Ser Leu Leu His Ser Asn Leu Asn Thr Tyr Leu Tyr
1               5                   10                  15

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Ile Ser Pro Gly Gly Asp Tyr Ile Tyr Tyr Ala Asp Ser Val Lys
1               5                   10                  15

Gly

<210> SEQ ID NO 19
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Leu Asn Thr Tyr Leu Tyr Trp Phe Leu Gln Lys Pro Gly Gln Ser
        35                  40                  45

Pro Gln Ile Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Pro Gly Thr Lys Leu Glu Ile Lys
            100                 105                 110

Arg

<210> SEQ ID NO 20
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Ile Arg Gln Ala Pro Gly Lys Gly Leu Glu Trp Val
        35                  40                  45

Ser Tyr Ile Ser Pro Gly Gly Asp Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Thr

<210> SEQ ID NO 21
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Leu Asn Thr Tyr Leu Tyr Trp Phe Leu Gln Lys Pro Gly Gln Ser
        35                  40                  45

Pro Gln Ile Leu Ile Tyr Arg Met Ser Asn Leu Ala Ser Gly Val Pro
    50                  55                  60

```
Asp Arg Phe Ser Gly Ser Gly Ser Gly Thr Ala Phe Thr Leu Lys Ile
 65                  70                  75                  80

Ser Arg Val Glu Ala Glu Asp Val Gly Val Tyr Tyr Cys Met Gln His
             85                  90                  95

Leu Glu Tyr Pro Phe Thr Phe Gly Pro Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 22
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
             20                  25                  30

Ala Met Ser Trp Ile Arg Gln Ala Pro Gly Lys Gly Leu Glu Trp Val
         35                  40                  45

Ser Tyr Ile Ser Pro Gly Gly Asp Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Thr Thr Asp Arg Arg His Tyr Gly Ser Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
            195                 200                 205
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 23
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Thr Leu Ser
            20                  25                  30

Ala Ser Val Gly Asp Arg Val Thr Ile Thr Cys Ser Ala Ser Gln Gly
        35                  40                  45

Ile Ser Asn Tyr Leu Asn Trp Tyr Gln Gln Lys Pro Gly Lys Ala Pro
    50                  55                  60

Lys Leu Leu Ile Gln Tyr Thr Ser Leu Leu His Ser Gly Val Pro Ser
65                  70                  75                  80

Arg Phe Ser Gly Ser Gly Ser Gly Thr Glu Tyr Thr Leu Thr Ile Ser
                85                  90                  95
```

```
Ser Leu Gln Pro Asp Asp Phe Ala Thr Tyr Phe Cys Gln Gln Tyr Ser
            100                 105                 110

Lys Phe Pro Arg Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 24
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Ser Ala Ser Gln Gly
        35                  40                  45

Ile Ser Asn Tyr Leu Asn Trp Tyr Gln Gln Lys Pro Gly Lys Ala Pro
    50                  55                  60

Lys Leu Leu Ile Gln Tyr Thr Ser Leu Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln Gln Tyr Ser
            100                 105                 110

Lys Phe Pro Arg Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220
```

Val Thr Lys Ser Phe Asn Arg Gly Glu Cys
225                 230

<210> SEQ ID NO 25
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Asp Pro Lys Gly Ser Leu Ser Trp Arg Ile Leu Leu Phe Leu Ser
1               5                   10                  15

Leu Ala Phe Glu Leu Ser Tyr Gly Gln Ile Gln Leu Val Gln Ser Gly
            20                  25                  30

Ser Glu Leu Lys Lys Pro Gly Ala Ser Val Lys Val Ser Cys Lys Ala
        35                  40                  45

Phe Gly Tyr Thr Phe Thr Asn Tyr Gly Met Asn Trp Val Lys Gln Ala
    50                  55                  60

Pro Gly Gln Gly Leu Lys Trp Met Gly Trp Ile Asn Thr Tyr Thr Gly
65                  70                  75                  80

Glu Pro Thr Tyr Ala Gln Gly Phe Thr Gly Arg Phe Val Phe Ser Leu
                85                  90                  95

Glu Thr Ser Val Ser Thr Ala Tyr Leu Gln Ile Ser Ser Leu Lys Ala
            100                 105                 110

Glu Asp Thr Ala Val Tyr Phe Cys Ala Arg Asn Tyr Gly Asn Tyr Leu
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala

```
            340                 345                 350
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly
465                 470

<210> SEQ ID NO 26
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Pro Lys Gly Ser Leu Ser Trp Arg Ile Leu Leu Phe Leu Ser
1               5                   10                  15

Leu Ala Phe Glu Leu Ser Tyr Gly Gln Ile Gln Leu Val Gln Ser Gly
            20                  25                  30

Ala Glu Val Lys Lys Pro Gly Ala Ser Val Lys Val Ser Cys Lys Ala
        35                  40                  45

Phe Gly Tyr Thr Phe Thr Asn Tyr Gly Met Asn Trp Val Lys Gln Ala
50                  55                  60

Pro Gly Gln Gly Leu Lys Trp Met Gly Trp Ile Asn Thr Tyr Thr Gly
65                  70                  75                  80

Glu Pro Thr Tyr Ala Asp Asp Phe Lys Gly Arg Val Thr Phe Thr Leu
                85                  90                  95

Glu Thr Ser Ile Ser Thr Ala Tyr Met Glu Leu Ser Arg Leu Arg Ser
            100                 105                 110

Asp Asp Thr Ala Val Tyr Phe Cys Ala Arg Asn Tyr Gly Asn Tyr Leu
        115                 120                 125

Phe Asp Tyr Trp Gly Gln Gly Thr Leu Val Thr Val Ser Ser Ala Ser
130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
210                 215                 220
```

```
Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
            245                 250                 255

Pro Glu Leu Leu Gly Gly Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly
465                 470

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Leu Lys Leu Leu Ile
        35                  40                  45

Gln Tyr Thr Ser Leu Leu His Ser Gly Val Pro Ser Arg Phe Ser Gly
    50                  55                  60

Ser Gly Ser Gly Thr Glu Tyr Ser Leu Thr Ile Ser Asn Leu Glu Pro
65                  70                  75                  80

Glu Asp Ile Ala Thr Tyr Phe Cys Gln Gln Tyr Ser Lys Phe Pro Arg
                85                  90                  95

Thr Phe Gly Gly Gly Thr Lys Leu Glu Ile Lys Arg
            100                 105
```

```
<210> SEQ ID NO 28
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Ile Gln Leu Val Gln Ser Gly Pro Glu Leu Lys Lys Ser Gly Glu
1               5                   10                  15

Thr Val Lys Ile Ser Cys Lys Ala Phe Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn His Leu Lys Asn Glu Asp Thr Ala Thr Tyr Phe Cys
                85                  90                  95

Ala Arg Asn Tyr Gly Asn Tyr Leu Phe Asp Tyr Trp Gly Gln Gly Thr
            100                 105                 110

Thr Leu Thr Val Ser Ser
        115

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Ser Gln Gly Ile Ser Asn Tyr Leu Asn
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Ser Leu Leu His Ser Gly
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Tyr Ser Lys Phe Pro Arg Thr
1               5
```

```
<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Tyr Thr Phe Thr Asn Tyr Gly Met Asn
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Asn Thr Tyr Thr Gly Glu Pro Thr Tyr Ala Asp Asp Phe Lys Gly
1               5                   10                  15

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Tyr Gly Asn Tyr Leu Phe Asp Tyr
1               5
```

ANTI-MICA/B ANTIBODIES THAT BLOCK MICA/B SHEDDING AND METHODS OF USE

CROSS REFERENCE

This application is a bypass continuation of co-pending PCT Application No. PCT/US2019/044234, filed on Jul. 30, 2019, which claims the benefit of U.S. Provisional Application No. 62/712,608 filed Jul. 31, 2018, which is incorporated by reference herein in its entirety.

INCORPORATION BY REFERENCE OF SEQUENCE LISTING

This application contains a Sequence listing that has been submitted in a computer readable format and is hereby incorporated by reference in its entirety. The ASCII text file, created on Feb. 21, 2024, is named 67252US02_SL and is 32,756 bytes in size.

SUMMARY

Disclosed herein, are monoclonal antibodies that specifically bind to MICA/B and thereby modulating an immune response against disease cells.

Disclosed herein, in certain embodiments, are monoclonal antibodies or an antigen-binding fragments thereof, comprising a light chain comprising an amino acid sequence at least 80% identical to an amino acid sequence set forth as SEQ ID NO: 21, SEQ ID NO: 23, or SEQ ID NO:24. In some embodiments, the monoclonal antibodies or an antigen-binding fragments thereof further comprises a heavy chain comprising an amino acid sequence at least 80% identical to an amino acid sequence set forth as SEQ ID NO: 22, SEQ ID NO: 25, or SEQ ID NO: 26.

Disclosed herein, in certain embodiments, are monoclonal antibodies or an antigen-binding fragments thereof, comprising a light chain variable domain (VL) comprising an amino acid sequence at least 80% identical to an amino acid sequence set forth as SEQ ID NO: 7, SEQ ID NO: 15, or SEQ ID NO: 19. Disclosed herein, in certain embodiments, are monoclonal antibodies or an antigen-binding fragments thereof, comprising a light chain variable domain (VL) comprising an amino acid sequence at least 90% identical to an amino acid sequence set forth as SEQ ID NO: 7, SEQ ID NO: 15, or SEQ ID NO: 19. Disclosed herein, in certain embodiments, are monoclonal antibodies or an antigen-binding fragments thereof, comprising a light chain variable domain (VL) comprising an amino acid sequence at least 95% identical to an amino acid sequence set forth as SEQ ID NO: 7, SEQ ID NO: 15, or SEQ ID NO: 19. Disclosed herein, in certain embodiments, are monoclonal antibodies or an antigen-binding fragments thereof, comprising a light chain variable domain (VL) comprising an amino acid sequence at least 99% identical to an amino acid sequence set forth as SEQ ID NO: 7, SEQ ID NO: 15, or SEQ ID NO: 19. Disclosed herein, in certain embodiments, are monoclonal antibodies or an antigen-binding fragments thereof, comprising a light chain variable domain (VL) comprising an amino acid sequence 100% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO: 16, or SEQ ID NO: 20. In some instances, the monoclonal antibody or antigen-binding fragment thereof comprises a heavy chain variable domain (VH) comprising an amino acid sequence at least 90% identical to an amino acid sequence set forth as SEQ ID NO: 8, SEQ ID NO: 16, or SEQ ID NO: 20. In some instances, the monoclonal antibody or antigen-binding fragment thereof comprises a heavy chain variable domain (VH) comprising an amino acid sequence at least 95% identical to an amino acid sequence set forth as SEQ ID NO: 8, SEQ ID NO: 16, or SEQ ID NO: 20. In some instances, the monoclonal antibody or antigen-binding fragment thereof comprises a heavy chain variable domain (VH) comprising an amino acid sequence at least 99% identical to an amino acid sequence set forth as SEQ ID NO: 8, SEQ ID NO: 16, or SEQ ID NO: 20. In some instances, the monoclonal antibody or antigen-binding fragment thereof comprises a heavy chain variable domain (VH) comprising an amino acid sequence 100% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof comprises heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab')2, or a disulfide linked Fv. In some instances, the monoclonal antibody or antigen-binding fragment thereof is an IgG or IgM. In some instances, the monoclonal antibody or antigen-binding fragment thereof is humanized or chimeric.

Disclosed herein, in certain embodiments, are monoclonal antibodies or an antigen-binding fragments thereof, comprising a heavy chain variable domain (VH) comprising an amino acid sequence at least 80% identical to an amino acid sequence set forth as SEQ ID NO: 8, SEQ ID NO: 16, or SEQ ID NO: 20. Disclosed herein, in certain embodiments, are monoclonal antibodies or an antigen-binding fragments thereof, comprising a heavy chain variable domain (VH) comprising an amino acid sequence at least 90% identical to an amino acid sequence set forth as SEQ ID NO: 8, SEQ ID NO: 16, or SEQ ID NO: 20. Disclosed herein, in certain embodiments, are monoclonal antibodies or an antigen-binding fragments thereof, comprising a heavy chain variable domain (VH) comprising an amino acid sequence at least 95% identical to an amino acid sequence set forth as SEQ ID NO: 8, SEQ ID NO: 16, or SEQ ID NO: 20. Disclosed herein, in certain embodiments, are monoclonal antibodies or an antigen-binding fragments thereof, comprising a heavy chain variable domain (VH) comprising an amino acid sequence at least 99% identical to an amino acid sequence set forth as SEQ ID NO: 8, SEQ ID NO: 16, or SEQ ID NO: 20. Disclosed herein, in certain embodiments, are monoclonal antibodies or an antigen-binding fragments thereof, comprising a heavy chain variable domain (VH) comprising an amino acid sequence 100% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19. In some instances, the monoclonal antibody or antigen-binding fragment thereof comprises a light chain variable domain (VL) comprising an amino acid sequence at least 90% identical to an amino acid sequence set forth as SEQ ID NO: 7, SEQ ID NO: 15, or SEQ ID NO: 19. In some instances, the monoclonal antibody or antigen-binding fragment thereof comprises a light chain variable domain (VL) comprising an amino acid sequence at least 95% identical to an amino acid sequence set forth as SEQ ID NO: 7, SEQ ID NO: 15, or SEQ ID NO: 19. In some instances, the monoclonal antibody or antigen-binding fragment thereof comprises a light chain variable domain (VL) comprising an amino acid sequence at least 99% identical to an amino acid sequence set forth as SEQ ID NO: 7, SEQ ID NO: 15, or SEQ ID NO: 19. In some instances, the monoclonal antibody or antigen-binding fragment thereof comprises a light chain variable domain (VL) comprising an amino acid sequence 100% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to SEQ ID NO: 8 and a light chain variable domain (VL) comprising an amino acid sequence at least 80% identical to SEQ ID NO: 7. In some instances, the monoclonal antibody or antigen-binding fragment thereof comprises a heavy chain variable domain (VH) comprising an amino acid sequence at least 80% identical to SEQ ID NO: 16 and a light chain variable domain (VL) comprising an amino acid sequence at least 80% identical to SEQ ID NO: 15. In some instances, the monoclonal antibody or antigen-binding fragment thereof comprises a heavy chain variable domain (VH) comprising an amino acid sequence at least 80% identical to SEQ ID NO: 20 and a light chain variable domain (VL) comprising an amino acid sequence at least 80% identical to SEQ ID NO: 19. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab'h, or a disulfide linked Fv. In some instances, the monoclonal antibody or antigen-binding fragment thereof is an IgG or IgM. In some instances, the monoclonal antibody or antigen-binding fragment thereof is humanized or chimeric.

Disclosed herein, in certain embodiments, are monoclonal antibodies or an antigen-binding fragments thereof, comprising a light chain complementarity determining region (CDR) having an amino acid sequence at least 80% identical to at least one of the amino acid sequences set forth as SEQ ID NOS: 1-3, 9-11, and 17, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are monoclonal antibodies or an antigen-binding fragments thereof, comprising a light chain complementarity determining region (CDR) having an amino acid sequence at least 90% identical to at least one of the amino acid sequences set forth as SEQ ID NOS: 1-3, 9-11, and 17, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are monoclonal antibodies or an antigen-binding fragments thereof, comprising a light chain complementarity determining region (CDR) having an amino acid sequence at least 95% identical to at least one of the amino acid sequences set forth as SEQ ID NOS: 1-3, 9-11, and 17, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are monoclonal antibodies or an antigen-binding fragments thereof, comprising a light chain complementarity determining region (CDR) having an amino acid sequence at least 99% identical to at least one of the amino acid sequences set forth as SEQ ID NOS: 1-3, 9-11, and 17, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are monoclonal antibodies or an antigen-binding fragments thereof, comprising a light chain complementarity determining region (CDR) having an amino acid sequence 100% identical to at least one of the amino acid sequences set forth as SEQ ID NOS: 1-3, 9-11, and 17, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. In some instances, the monoclonal antibody or antigen-binding fragment thereof comprises a heavy chain complementarity determining region (CDR) having an amino acid sequence at least 80% identical to at least one of the amino acid sequences set forth as SEQ ID NOS: 4-6, 12-14, and 18. In some instances, the monoclonal antibody or antigen-binding fragment thereof comprises a heavy chain complementarity determining region (CDR) having an amino acid sequence at least 90% identical to at least one of the amino acid sequences set forth as SEQ ID NOS: 4-6, 12-14, and 18. In some instances, the monoclonal antibody or antigen-binding fragment thereof comprises a heavy chain complementarity determining region (CDR) having an amino acid sequence at least 95% identical to at least one of the amino acid sequences set forth as SEQ ID NOS: 4-6, 12-14, and 18. In some instances, the monoclonal antibody or antigen-binding fragment thereof comprises a heavy chain complementarity determining region (CDR) having an amino acid sequence at least 99% identical to at least one of the amino acid sequences set forth as SEQ ID NOS: 4-6, 12-14, and 18. In some instances, the monoclonal antibody or antigen-binding fragment thereof comprises a heavy chain complementarity determining region (CDR) having an amino acid sequence 100% identical to at least one of the amino acid sequences set forth as SEQ ID NOS: 4-6, 12-14, and 18. In some instances, the monoclonal antibody or antigen-binding fragment thereof comprises a light chain complementarity determining region 1 (CDR1) having an amino acid sequence at least 80% identical to one of SEQ ID NO: 1, SEQ ID NO: 9, or SEQ ID NO: 17, a light chain complementarity determining region 2 (CDR2) having an amino acid sequence at least 80% identical to one of SEQ ID NOS: SEQ ID NO: 2, or SEQ ID NO: 10, a light chain complementarity determining region 3 (CDR3) having an amino acid sequence at least 80% identical to one of SEQ ID NO: 3, or SEQ ID NO: 11, a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, and a heavy chain complementarity determining region 3 (CDR3) having an amino acid sequence at least 80% identical to one of SEQ ID NO: 6, or SEQ ID NO: 14. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO:11. In some instances, the monoclonal antibody or antigen-binding fragment thereof comprises at least one of a light chain complementarity determining region 1 (CDR1) having an amino acid sequence at least 80% identical to SEQ ID NO: 17, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, or SEQ ID NO: 15; and a heavy chain variable domain (VH) comprising an amino acid sequence at least 80% identical to an amino acid sequence set forth as SEQ ID NO: 8, or SEQ ID NO: 16. In some instances, the monoclonal antibody or antigen-binding fragment thereof comprises a heavy chain variable domain (VH) comprising an amino acid sequence at least 80% identical to an amino acid sequence set forth as SEQ ID NO: 8, or SEQ ID NO: 16; and a light chain variable domain (VL) comprising an amino acid sequence at least 80% identical to an amino acid sequence set forth as SEQ ID NO: 7, or SEQ ID NO: 15. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof comprises heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab'h, or a disulfide linked Fv. In some instances, the monoclonal antibody or antigen-binding fragment thereof is an IgG or IgM. In some instances, the monoclonal antibody or antigen-binding fragment thereof is humanized or chimeric.

Disclosed herein, in certain embodiments, are monoclonal antibodies or an antigen-binding fragments thereof, comprising a heavy chain complementarity determining region (CDR) having an amino acid sequence at least 80% identical to at least one of the amino acid sequences set forth as SEQ ID NOS: 4-6, 12-14, and 18, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are monoclonal antibodies or an antigen-binding fragments thereof, comprising a heavy chain complementarity determining region (CDR) having an amino acid sequence at least 90% identical to at least one of the amino acid sequences set forth as SEQ ID NOS: 4-6, 12-14, and 18, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are monoclonal antibodies or an antigen-binding fragments thereof, comprising a heavy chain complementarity determining region (CDR) having an amino acid sequence at least 95% identical to at least one of the amino acid sequences set forth as SEQ ID NOS: 4-6, 12-14, and 18, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are monoclonal antibodies or an antigen-binding fragments thereof, comprising a heavy chain complementarity determining region (CDR) having an amino acid sequence at least 99% identical to at least one of the amino acid sequences set forth as SEQ ID NOS: 4-6, 12-14, and 18, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are monoclonal antibodies or an antigen-binding fragments thereof, comprising a heavy chain complementarity determining region (CDR) having an amino acid sequence 100% identical to at least one of the amino acid sequences set forth as SEQ ID NOS: 4-6, 12-14, and 18, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. In some instances, the monoclonal antibody or antigen-binding fragment comprises a light chain complementarity determining region (CDR) having an amino acid sequence at least 80% identical to at least one of the amino acid sequences set forth as SEQ ID NOS: 1-3, 9-11, and 17. In some instances, the monoclonal antibody or antigen-binding fragment comprises a light chain complementarity determining region (CDR) having an amino acid sequence at least 90% identical to at least one of the amino acid sequences set forth as SEQ ID NOS: 1-3, 9-11, and 17. In some instances, the monoclonal antibody or antigen-binding fragment comprises a light chain complementarity determining region (CDR) having an amino acid sequence at least 95% identical to at least one of the amino acid sequences set forth as SEQ ID NOS: 1-3, 9-11, and 17. In some instances, the monoclonal antibody or antigen-binding fragment comprises a light chain complementarity determining region (CDR) having an amino acid sequence at least 99% identical to at least one of the amino acid sequences set forth as SEQ ID NOS: 1-3, 9-11, and 17. In some instances, the monoclonal antibody or antigen-binding fragment comprises a light chain complementarity determining region (CDR) having an amino acid sequence 100% identical to at least one of the amino acid sequences set forth as SEQ ID NOS: 1-3, 9-11, and 17. In some instances, the monoclonal antibody or antigen-binding fragment thereof comprises a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, a heavy chain complementarity determining region 3 (CDR3) having an amino acid sequence at least 80% identical to one of SEQ ID NO: 6, or SEQ ID NO: 14, a light chain complementarity determining region 1 (CDR1) having an amino acid sequence at least 80% identical to one of SEQ ID NO: 1, SEQ ID NO: 9, or SEQ ID NO: 17, a light chain complementarity determining region 2 (CDR2) having an amino acid sequence at least 80% identical to one of SEQ ID NO: 2, or SEQ ID NO: 10, and a light chain complementarity determining region 3 (CDR3) having an amino acid sequence at least 80% identical to one of SEQ ID NO: 3, or SEQ ID NO: 11. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO: 11. In some instances, the monoclonal antibody or antigen-binding fragment thereof comprises at least one of a light chain complementarity determining region 1 (CDR1) having an amino acid sequence at least 80% identical to SEQ ID NO: 17, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO:20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO:19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO:20; and a light chain variable domain (VL) comprising an amino acid sequence at least 80% identical to an amino acid sequence set forth as SEQ ID NO: 7, SEQ ID NO: 15, or SEQ ID NO:19. In some instances, the monoclonal antibody or antigen-binding fragment thereof comprises a light chain variable domain (VL) comprising an amino acid sequence at least 80% identical to an amino acid sequence set forth as SEQ ID NO: 7, or SEQ ID NO: 15; and a heavy chain variable domain (VH) comprising an amino acid sequence at least 80% identical to an amino acid sequence set forth as SEQ ID NO: 8, or SEQ ID NO: 16. In some instances, the monoclonal antibody or antigen-binding fragment thereof comprises a heavy chain variable domain (VH) comprising an amino acid sequence at least 80% identical to an amino acid sequence set forth as SEQ ID NO: 8 and a light chain variable domain (VL) comprising an amino acid sequence at least 80% identical to an amino acid sequence set forth as SEQ ID NO: 7. In some instances, the monoclonal antibody or antigen-binding fragment thereof comprises a heavy chain variable domain (VH) comprising an amino acid sequence at least 80% identical to an amino acid sequence set forth as SEQ ID NO: 16; and a light chain variable domain (VL) comprising an amino acid sequence at least 80% identical to an amino acid sequence set forth as SEQ ID NO: 15. In some instances, the monoclonal antibody or antigen-binding fragment thereof comprises a heavy chain variable domain (VH) comprising an amino acid sequence at least 80% identical to an amino acid sequence set forth as SEQ ID NO: 20; and a light chain variable domain (VL) comprising an amino acid sequence at least 80% identical to an amino acid sequence set forth as SEQ ID NO: 19. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO:24. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab'h, or a disulfide linked Fv. In some instances, the monoclonal antibody or antigen-binding fragment thereof is an IgG or IgM. In some instances, the monoclonal antibody or antigen-binding fragment thereof is humanized or chimeric.

Disclosed herein, in certain embodiments, are pharmaceutical compositions comprising: a monoclonal antibody or an antigen-binding fragment thereof according to any one of the disclosures herein; and a pharmaceutically acceptable carrier or excipient.

Disclosed herein, in certain embodiments, are methods of treating cancer in an individual in need thereof, comprising administering to the individual an effective amount of a monoclonal antibody or an antigen-binding fragment thereof comprising a light chain complementarity determining region (CDR) having an amino acid sequence at least 80% identical to at least one of the amino acid sequences set forth as SEQ ID NOS: 1-3, 9-11, and 17, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are methods of treating cancer in an individual in need thereof, comprising administering to the individual an effective amount of a monoclonal antibody or an antigen-binding fragment thereof comprising a heavy chain complementarity determining region (CDR) having an amino acid sequence at least 80% identical to at least one of the amino acid sequences set forth as SEQ ID NOS: 4-6, 12-14, and 18, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. In some instances, the monoclonal antibody or antigen-binding fragment thereof comprises (a) a light chain complementarity determining region (CDR) having an amino acid sequence at least 80% identical to at least one of the amino acid sequences set forth as SEQ ID NOS: 1-3, 9-11, and 17; and (b) a heavy chain complementarity determining region (CDR) having an amino acid sequence at least 80% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 90% identical to at least one of the amino acid sequences set forth as SEQ ID NOS: 1-3, 9-11, and 17; and (b) a heavy chain complementarity determining region (CDR) having an amino acid sequence at least 90% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 95% identical to at least one of the amino acid sequences set forth as SEQ ID NOS: 1-3, 9-11, and 17; and (b) a heavy chain complementarity determining region (CDR) having an amino acid sequence at least 95% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 99% identical to at least one of the amino acid sequences set forth as SEQ ID NOS: 1-3, 9-11, and 17; and (b) a heavy chain complementarity determining region (CDR) having an amino acid sequence at least 99% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence 100% identical to at least one of the amino acid sequences set forth as SEQ ID NOS: 1-3, 9-11, and 17; and (b) a heavy chain complementarity determining region (CDR) having an amino acid sequence 100% identical to at least one of the amino acid sequences set forth as SEQ ID NOS: 4-6, 12-14, and 18. In some instances, the monoclonal antibody or antigen-binding fragment thereof comprises a light chain complementarity determining region 1 (CDR1) having an amino acid sequence at least 80% identical to one of SEQ ID NO: 1, SEQ ID NO: 9, or SEQ ID NO: 17, a light chain complementarity determining region 2 (CDR2) having an amino acid sequence at least 80% identical to one of SEQ ID NOS: SEQ ID NO: 2, or SEQ ID NO: 10, a light chain complementarity determining region 3 (CDR3) having an amino acid sequence at least 80% identical to one of SEQ ID NO: 3, or SEQ ID NO: 11, a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, and a heavy chain complementarity determining region 3 (CDR3) having an amino acid sequence at least 80% identical to one of SEQ ID NO: 6, or SEQ ID NO: 14. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO:11. In some instances, the monoclonal antibody or antigen-binding fragment thereof comprises at least one of a light chain complementarity determining region 17 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19; and a heavy chain variable domain (VH) comprising an amino acid sequence at least 80% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab'h, or a disulfide linked Fv. In some instances, the monoclonal antibody or antigen-binding fragment thereof is an IgG or IgM. In some instances, the monoclonal antibody or antigen-binding fragment thereof is humanized or chimeric. In some instances, the monoclonal antibody or antigen-binding fragment thereof reduces level of soluble MICA protein, soluble MICB protein, or both. In some instances, the monoclonal antibody or antigen-binding fragment thereof reduces shedding of soluble MICA protein, soluble MICB protein, or both. In some instances, the monoclonal antibody or antigen-binding fragment thereof inhibits shedding of soluble MICA protein, soluble MICB protein, or both. In some instances, the cancer is hepatocellular carcinoma.

Disclosed herein, in certain embodiments, are methods of treating hepatocellular carcinoma in an individual in need thereof, comprising administering to the individual an effective amount of a monoclonal antibody or an antigen-binding fragment thereof comprising a light chain complementarity determining region (CDR) having an amino acid sequence at least 80% identical to at least one of the amino acid sequences set forth as SEQ ID NOS: 1-3, 9-11, and 17, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are methods of treating hepatocellular carcinoma in an individual in need thereof, comprising administering to the individual an effective amount of a monoclonal antibody or an antigen-binding fragment thereof comprising a heavy chain complementarity determining region (CDR) having an amino acid sequence at least 80% identical to at least one of the amino acid sequences set forth as SEQ ID NOS: 4-6, 12-14, and 18, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. In some instances, the monoclonal antibody or antigen-binding fragment thereof comprises (a) a light chain complementarity determining region (CDR) having an amino acid sequence at least 80% identical to at least one of the amino acid sequences set forth as SEQ ID NOS: 1-3, 9-11, and 17; and (b) a heavy chain complementarity determining region (CDR) having an amino acid sequence at least 80% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 90% identical to at least one of the amino acid sequences set forth as SEQ ID NOS: 1-3, 9-11, and 17; and (b) a heavy chain complementarity determining region (CDR) having an amino acid sequence at least 90% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 95% identical to at least one of the amino acid sequences set forth as SEQ ID NOS: 1-3, 9-11, and 17; and (b) a heavy chain complementarity determining region (CDR) having an amino acid sequence at least 95% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 99% identical to at least one of the amino acid sequences set forth as SEQ ID NOS: 1-3, 9-11, and 17; and (b) a heavy chain complementarity determining region (CDR) having an amino acid sequence at least 99% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence 100% identical to at least one of the amino acid sequences set forth as SEQ ID NOS: 1-3, 9-11, and 17; and (b) a heavy chain complementarity determining region (CDR) having an amino acid sequence 100% identical to at least one of the amino acid sequences set forth as SEQ ID NOS: 4-6, 12-14, and 18. In some instances, the monoclonal antibody or antigen-binding fragment thereof comprises a light chain complementarity determining region 1 (CDR1) having an amino acid sequence at least 80% identical to one of SEQ ID NO: 1, SEQ ID NO: 9, or SEQ ID NO: 17, a light chain complementarity determining region 2 (CDR2) having an amino acid sequence at least 80% identical to one of SEQ ID NOS: SEQ ID NO: 2, or SEQ ID NO: 10, a light chain complementarity determining region 3 (CDR3) having an amino acid sequence at least 80% identical to one of SEQ ID NO: 3, or SEQ ID NO: 11, a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, and a heavy chain complementarity determining region 3 (CDR3) having an amino acid sequence at least 80% identical to one of SEQ ID NO: 6, or SEQ ID NO: 14. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO:11. In some instances, the monoclonal antibody or antigen-binding fragment thereof comprises at least one of a light chain complementarity determining region 17 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19; and a heavy chain variable domain (VH) comprising an amino acid sequence at least 80% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab'h, or a disulfide linked Fv. In some instances, the monoclonal antibody or antigen-binding fragment thereof is an IgG or IgM. In some instances, the monoclonal antibody or fragment thereof is humanized or chimeric. In some instances, the monoclonal antibody or antigen binding fragment thereof reduces level of soluble MICA protein, soluble MICB protein, or both. In some instances, the monoclonal antibody or antigen binding fragment thereof reduces shedding of soluble MICA protein, soluble MICB protein, or both. In some instances, the monoclonal antibody or antigen binding fragment thereof inhibits shedding of soluble MICA protein, soluble MICB protein, or both.

Disclosed herein, in certain embodiments, are methods of reducing level of soluble MICA protein, soluble MICB protein, or both in an individual in need thereof, comprising administering to the individual an effective amount of a monoclonal antibody or an antigen-binding fragment thereof comprising a light chain complementarity determining region (CDR) having an amino acid sequence at least 80% identical to at least one of the amino acid sequences set forth as SEQ ID NOS: 1-3, 9-11, and 17, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. Disclosed herein, in certain embodiments, are methods of reducing level of soluble MICA protein, soluble MICB protein, or both in an individual in need thereof, comprising administering to the individual an effective amount of a monoclonal antibody or an antigen-binding fragment thereof comprising a heavy chain complementarity determining region (CDR) having an amino acid sequence at least 80% identical to at least one of the amino acid sequences set forth as SEQ ID NOS: 4-6, 12-14, and 18, wherein the monoclonal antibody does not have at least one CDR selected from the list comprising: SEQ ID NO: 29, SEQ ID NO: 30, SEQ ID NO: 31, SEQ ID NO: 32, SEQ ID NO: 33, and SEQ ID NO: 34. In some instances, the monoclonal antibody or antigen-binding fragment thereof comprises (a) a light chain complementarity determining region (CDR) having an amino acid sequence at least 80% identical to at least one of the amino acid sequences set forth as SEQ ID NOS: 1-3, 9-11, and 17; and (b) a heavy chain complementarity determining region (CDR) having an amino acid sequence at least 80% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 90% identical to at least one of the amino acid sequences set forth as SEQ ID NOS: 1-3, 9-11, and 17; and (b) a heavy chain complementarity determining region (CDR) having an amino acid sequence at least 90% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 95% identical to at least one of the amino acid sequences set forth as SEQ ID NOS: 1-3, 9-11, and 17; and (b) a heavy chain complementarity determining region (CDR) having an amino acid sequence at least 95% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 99% identical to at least one of the amino acid sequences set forth as SEQ ID NOS: 1-3, 9-11, and 17; and (b) a heavy chain complementarity determining region (CDR) having an amino acid sequence at least 99% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence 100% identical to at least one of the amino acid sequences set forth as SEQ ID NOS: 1-3, 9-11, and 17; and (b) a heavy chain complementarity determining region (CDR) having an amino acid sequence 100% identical to at least one of the amino acid sequences set forth as SEQ ID NOS: 4-6, 12-14, and 18. In some instances, the monoclonal antibody or antigen-binding fragment thereof comprises a light chain complementarity determining region 1 (CDR1) having an amino acid sequence at least 80% identical to one of SEQ ID NO: 1, SEQ ID NO: 9, or SEQ ID NO: 17, a light chain complementarity determining region 2 (CDR2) having an amino acid sequence at least 80% identical to one of SEQ ID NOS: SEQ ID NO: 2, or SEQ ID NO: 10, a light chain complementarity determining region 3 (CDR3) having an amino acid sequence at least 80% identical to one of SEQ ID NO: 3, or SEQ ID NO: 11, a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, and a heavy chain complementarity determining region 3 (CDR3) having an amino acid sequence at least 80% identical to one of SEQ ID NO: 6, or SEQ ID NO: 14. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO: 11. In some instances, the monoclonal antibody or antigen-binding fragment thereof comprises at least one of a light chain complementarity determining region 1 (CDR1) having an amino acid sequence at least 80% identical to SEQ ID NO: 17, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19; and a heavy chain variable domain (VH) comprising an amino acid sequence at least 80% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab'h, or a disulfide linked Fv. In some instances, the monoclonal antibody or antigen-binding fragment thereof is an IgG or IgM. In some instances, the monoclonal antibody or fragment thereof is humanized or chimeric. In some instances, the monoclonal antibody or antigen-binding fragment thereof reduces or inhibits shedding of soluble MICA protein, soluble MICB protein, or both, thereby reducing level of soluble MICA protein, soluble MICB protein, or both in the individual. In some instances, the individual has a cancer characterized by elevated levels of soluble MICA protein, soluble MICB protein, or both. In some instances, the cancer is hepatocellular carcinoma.

Disclosed herein, in certain embodiments, are monoclonal antibodies or an antigen-binding fragments thereof according to any one of disclosures herein for use in treating cancer in an individual in need thereof. Disclosed herein, in certain embodiments, are monoclonal antibodies or an antigen-binding fragments thereof according to any one of disclosures herein for use in preparation of a medicament for treating cancer in an individual in need thereof. In some instances, the cancer is hepatocellular carcinoma.

Disclosed herein, in certain embodiments, are monoclonal antibodies or an antigen-binding fragments thereof that competitively bind to MICA/B with an antibody comprising a light chain variable domain (VL) having an amino acid sequence at least about 80% identical to an amino acid sequence set forth as SEQ ID NO: 27. Disclosed herein, in certain embodiments, are monoclonal antibodies or an antigen-binding fragments thereof that competitively bind to MICA/B with an antibody comprising a heavy chain variable domain (VH) having an amino acid sequence at least about 80% identical to an amino acid sequence set forth as SEQ ID NO: 28.

BRIEF DESCRIPTION OF THE DRAWINGS

An understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1A:
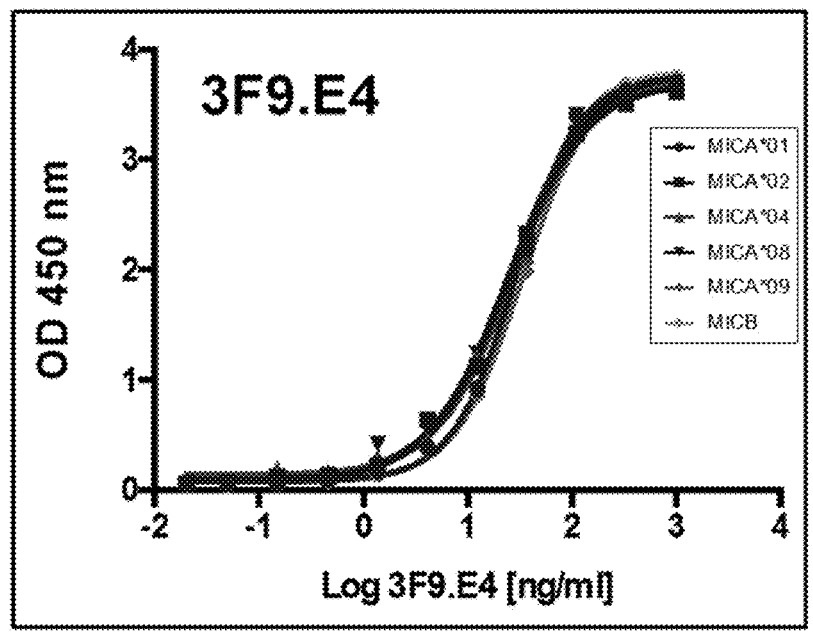
FIG. 1A-FIG. 1B exemplify binding of antibodies 3F9.E4 (FIG. 1A) and 16F10.C12 (FIG. 1B) to MICA/B alleles by ELISA.

Disclosed herein, in some embodiments, are monoclonal antibodies that bind specifically to MICA/B. In some embodiments, MICA/B antibodies herein bind to MICA/B proteins or fragments thereof and modulate immune response in an individual, thereby treating cancer (e.g. hepatocellular carcinoma).

Major histocompatibility complex class I-related chain A and B (MICA/B) are two stress-inducible ligands for natural killer cell (NK) receptor NKG2D and play an important role in mediating the cytotoxicity of NK and T cells. Soluble MICA/B shed by diseased cells (e.g. cancer cells) desensitizes NK and T cells through binding of NKG2D receptor, thereby suppressing the immune response. Accordingly, modulation of MICA/B is useful in modulating an immune response in an individual, for example, in an individual suffering from cancer. Antibodies binding to MICA/B and modulating its activity are desirable for the development of novel therapeutics for treatment of cancer.

Certain Terminology

As used herein "MICA/B" refers to MICA protein, MICB protein or both MICA and MICB proteins, including their variants, isoforms, and species homologs of human MICA/B.

As used herein "antibody" refers to a glycoprotein which exhibits binding specificity to a specific antigen. An antibody often comprises a variable domain and a constant domain in each of a heavy chain and a light chain. Accordingly, most antibodies have a heavy chain variable domain (VH) and a light chain variable domain (VL) that together form the portion of the antibody that binds to the antigen. Within each variable domain are three complementarity determining regions (CDR) which form loops in the heavy chain variable domain (VH) and light chain variable domain (VL) that contact the surface of the antigen. Antibodies herein also include "antigen binding portion" or fragments of the antibody that are capable of binding to the antigen.

As used herein "chimeric" antibodies are antibodies having a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see e.g., Morrison et al., Proc. Natl. Acad. Sci. USA 81:6851-6855 (1984)). "Humanized antibodies" herein refers chimeric antibodies having human sequences substituted in the antibody sequence.

The terms "recipient", "individual", "subject", "host", and "patient", are used interchangeably herein and in some cases, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, the terms "treatment," "treating," and the like, in some cases, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with diseases (e.g. cancer). The term "therapeutic effect" refers to the reduction, elimination, or prevention of the disease, symptoms of the disease, or side effects of the disease in the subject.

A "therapeutically effective amount" in some cases means the amount that, when administered to a subject for treating a disease, is sufficient to effect treatment for that disease.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO:Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

MICA/B

Disclosed herein, in some embodiments, are monoclonal antibodies that bind specifically to MICA/B. Further disclosed herein, in some embodiments, are monoclonal antibodies that competitively bind to MICA/B.

Major Histocompatibility Complex (MHC) class I Chain-related gene A and gene B protein (MICA/B) are glycosylated, polymorphic and membrane-anchored non-classical MHC class I proteins. MICA/B are related to MHC class I and have similar domain structure comprising three extracellular Ig-like domains (alpha-1, alpha-2 and alpha-3), a transmembrane domain and a C-terminal cytoplasmic tail. However, MICA/B do not associate with P2-microglobulin, lack a CD8 binding site and do not present any antigens.

MICA/Bare ligands to C-type lectin-like activating receptor Natural Killer Group 2D (NKG2D) on immune effector cells, including NK, NKT and both αβ and γδ CD8+ T cells. The interaction of MICA/B and NKG2D plays a role in tumor surveillance, and immune response.

MICA/B proteins are expressed normally at low levels in normal cells, but are induced to higher levels in stressed or transformed cells (e.g. cancer cells). The interaction of NKG2D-bearing immune effector cells with stressed or diseased cells expressing MICA/B ligands on the cell surface creates a cellular immune response against the stressed/diseased cell that culminates in the death of the MICA/B expressing cells. In cancer cells, the truncated MICA/B proteins (proteins that lack the transmembrane domain and cytoplasmic tail but retain the three extracellular domain comprising alpha-1, -2 and -3 domains) are frequently shed into the blood by the action of proteases and results in the down-modulation (receptor internalization) of its intended receptor, NKG2D, on effector immune cells. In some instances, MICA/B glycoproteins are produced intracellularly that are not routinely destined to become cell surface membrane-bound, but instead are incorporated within exosomes and released outside the cell where interaction with NKG2D receptors on immune cells occurs. These truncated or soluble MICA/B ligands shed from the surface of cancer cells function like decoy molecules and lead to down-modulation of the NKG2D receptor on immune effector cells such as NK, NKT and various CD8+ T cells. In some instances, the formation of soluble MICA/B leads to the unusual situation where the effectors of the innate defense system, whose natural role is to seek and destroy transformed cells, are shut down by the immunosuppressive actions of these decoy ligand molecules, thereby enabling the cancer cells to hide from the immune system and to grow unchecked.

Hepatocellular Carcinoma (HCC)

In some embodiments, anti-MICA/B antibodies disclosed herein bind to MICA/B proteins or fragments thereof and modulate immune response in an individual, thereby treating cancer (e.g. hepatocellular carcinoma).

Hepatocellular carcinoma (HCC) is a primary malignancy of the liver and occurs predominantly in individuals with underlying chronic liver disease and cirrhosis. Tumors progress with local expansion, intrahepatic spread, and distant metastases. Hepatitis B and Hepatitis C predisposes individuals to the development of chronic liver disease and subsequent development of HCC. Obesity, diabetes, and alcohol abuse are some other causes that predispose individuals to the subsequent development of HCC.

Anti-MICA/B Antibodies

Provided herein are antibodies that specifically bind to MICAS proteins. In some embodiments, anti-MICAS antibodies comprise at least one heavy chain and anti-MICAS antibodies comprise at least one light chain. In some embodiments, anti-MICAS antibodies comprise at least one heavy chain comprising a heavy chain variable domain (VH) and at least one light chain comprising a light chain variable domain (VL). Each VH and VL comprises three complementarity determining regions (CDR). The amino acid sequences of the VH and VL and the CDRs determine the antigen binding specificity and antigen binding strength of the antibody. The amino acid sequences of the Heavy and Light chains, VH and VL and the CDRs are summarized in Table 1.

TABLE 1

Anti-MICA/B Monoclonal Antibody Sequences

| | SEQUENCE | SEQ ID NO: |
|---|---|---|
| 3F9.E4 Light Chain CDR1 | RSSKSLLHSNGNTYLY | 1 |
| 3F9.E4 Light Chain CDR2 | RMSNLAS | 2 |
| 3F9.E4 Light Chain CDR3 | MQHLEYPFT | 3 |
| 3F9.E4 Heavy Chain CDR1 | GFTFSNYAMS | 4 |
| 3F9.E4 Heavy Chain CDR2 | YISPGGDYIYYADTVKG | 5 |
| 3F9.E4 Heavy Chain CDR3 | DRRHYGSYAMDY | 6 |
| 3F9.E4 Light Chain Variable domain | DIVMTQAAPSVPVTPGESVSISCRSSKSLLHSNGNTYLYWFLQRPGQS PQLLIYRMSNLASGVPDRFSGSGSGTAFTLRISRVEAEDVGVYYCMQ HLEYPFTFGSGTKLEIK | 7 |
| 3F9.E4 Heavy Chain Variable domain | EVQLQESGEGLVKPGGSLKLSCAASGFTESNYAMSWVRQTPEKRLE WVAYISPQGQDYIYYADTVKGRFTISRDNARNTLYLOMSSLKSEDTA MYYCTTDRRHYGSYAMDYWGQGISVTVSS | 8 |
| 16F10.C12 Light Chain CDR1 | TASSSVSSNYLH | 9 |
| 16F10.C12 Light Chain CDR2 | TTSNLAS | 10 |
| 16F10.C12 Light Chain CDR3 | HQFHRSPFT | 11 |

TABLE 1-continued

Anti-MICA/B Monoclonal Antibody Sequences

| | SEQUENCE | SEQ ID NO: |
|---|---|---|
| 16F10.C12 Heavy Chain CDR1 | GFSLTAFGVN | 12 |
| 16F10.C12 Heavy Chain CDR2 | MIWGDGNTDYNSTLRS | 13 |
| 16F10.C12 Heavy Chain CDR3 | ETYYGNYAGLGY | 14 |
| 16F10.C12 Light Chain Variable domain | QIVLTQSPAIMSASIGERVTMTCTASSSVSSNYLHWYQQKPRSSPKL WIYTTSNLASGVPTRFSGSGSGTSYSLTISSMEAEDAATYYCHQFHRS PFTFGSGTKLEIK | 15 |
| 16F10.C12 Heavy Chain Variable domain | EVQLQESGPGLVAPSQSLSITCTVSGFSLTAFGVNWVRQPPGKGLEW LGMIWGDGNTDYNSTLRSRLSISKDNSKSQVFLKLNSLQTDDTARYF CARETYYGNYAGLGYWGQGTLVTVSA | 16 |
| 3F9HIL3L Light Chain CDR1 | RSSKSLLHSNLNTYLY | 17 |
| 3F9HIL3L Light Chain CDR2 | RMSNLAS | 2 |
| 3F9HIL3L Light Chain CDR3 | MQHLEYPFT | 3 |
| 3F9HIL3L Heavy Chain CDR1 | GFTFSNYAMS | 4 |
| 3F9HIL3L Heavy Chain CDR2 | YISPGGDYTYYADSVKG | 18 |
| 3F9HIL3L Heavy Chain CDR3 | DRRHYGSYAMDY | 6 |
| 3F9HIL3L Light Chain Variable domain | DIVMTQSPLSLPVTPGEPASISCRSSKSLLHSNLNTYLYWFLQKPGQS PQILIYRMSNLASGVPDRFSGSGSGTAFTLKISRVEAEDVGVYYCMQ HLEYPFTPGPGTKLEIKR | 19 |
| 3F9HIL3L Heavy Chain Variable domain | QVQLVESGGGLVKPGGSLRLSCAASGFTFSNYAMSWIRQAPGKGLE WVSYISPGGDYIYYADSVKGRFTISRDNAKNSLYLQMNSLRAEDTA VYYCTT | 20 |
| 3F9HIL3L Light Chain | DIVMTQSPLSLPVTPGEPASISCRSSKSLLHSNLNTYLYWFLQKPGQS PQILIYRMSNLASGVPDRFSGSGSGTAFTLKISRVEAEDVGVYYCMQ HLEYPFTFGPGTKLEIKRTVAAPSVFIFPPSDEQLKSGTASVVCLLNNF YPREAKVQWKVDNALQSGNSQESVTEQDSKDSTYSLSSTLTLSKAD YEKHKVYACEVTHQGLSSPVTKSFNRGEC* | 21 |
| 3F9HIL3L Heavy Chain | QVQLVESGGGLVKPGGSLRLSCAASGFTFSNYAMSWIRQAPGKGLE WVSYISPGGDYIYYADSVKGRFTISRDNAKNSLYLQMNSLRAEDTA VYYCTTDRRHYGSYAMDYWGQGTLVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKARGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPG** | 22 |
| PDI-1 humanized LC5 Light Chain | METDTLLLWVLLLWVPGSTGDIQMTQSPSTLSASVGDRVTITCSASQ GISNYLNWYQQKPGKAPKLLIQYTSLLHSGVPSRPSGSGSGTEYTLTI SSLQPDDFATYFCQQYSKFFRTFGGGTKVEIKRTVAAPSVFIFPPSDE QLKSGTASVVCLLNNFYPREAKVQWKVDNALQSGNSQESVTEQDS KDSTYSLSSTLTLSKADYEKHKVYACEVTHQGLSSPVTKSFNRGEC* | 23 |
| PDI-1 humanized LC4 Light Chain | METDTLLLWVLLLWVPGSTGDIQMTQSPSSLSASVGDRVTITCSASQ GISNYLNWYQQKPGKAPKLLIQYTSLLHSGVPSRFSGSGSGTDYTLTI SSLQPEDFATYFCQQYSKFPRTFGGGTKVEIKRTVAAPSVFIFPPSDEQ LKSGTASVVCLLNNFYPREAKVQWKVDNALQSGNSQESVTEQDSK DSTYSLSSTLTLSKADYEKHKVYACEVTHQGLSSPVTKSFNRGEC* | 24 |

TABLE 1-continued

Anti-MICA/B Monoclonal Antibody Sequences

| | SEQUENCE | SEQ ID NO: |
|---|---|---|
| PDI-1 humanized HC4 Heavy Chain | MDPKGSLSWRILLFLSLAFELSYGQIQLVQSGSELKKPGASVKVSCK AFGYTFTNYGMNWVKQAPGQGLKWMGWINTYTGEPTYAQGFTGR FVFSLETSVSTAYLQISSLKAEDTAVYFCARNYGNYLFDYWGQGTL VTVSSASTKGPSVFPLAPSSKSTSGGTAALGCLVKDYFPEPVTVSWN SGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISR TPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSREEMTKNQVSLTCLVKGFYPSDIAVEWESNGQPENNYK TTPPVLDSDGSFFLYSKLTVDKSRWQQGNFSCSVMHEALHNHYTQ KSLSLSPG* | 25 |
| PDI-1 humanized HC6 Heavy Chain | MDPKGSLSWRILLFLSLAFELSYGQIQLVQSGAEVKKPGASVKVSCK AFGYTFTNYGMNWVKQAPGQGLKWMGWINTYTGEPTYADDFKGR VTFTLETSISTAYMELSRLRSDDTAVYFCARNYGNYLFDYWGQGTL VTVSSASTKGPSVFPLAPSSKSTSGGTAALGCLVKDYFPEPVTVSWN SGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISR TPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSREEMTKNQVSLTCLVKGFYPSDIAVEWESNGQPENNYK TTPPVLDSDGSFFLYSKLTVDKSRWQQGNVFSCSVMHEALHNHYTQ KSLSLSPG* | 26 |

In some embodiments, the antibodies specifically bind to a MICA protein. In some embodiments, the antibodies specifically bind to a MICB protein. In some embodiments, the antibodies specifically bind to both MICA and MICB protein. In some embodiments, the antibodies bind to an alpha-3 domain of a MICA protein. In some embodiments, the antibodies bind to an alpha-3 domain of a MICB protein. In some embodiments, the antibodies bind to an alpha-3 domain of both MICA and MICB protein. In some embodiments, the antibodies bind to a MICA protein that is membrane-bound MICA protein. In some embodiments, the antibodies bind to a MICA protein that is soluble MICA protein. In some embodiments, the antibodies bind to a MICA protein that is both membrane-bound MICA protein and soluble MICA protein. In some embodiments, the antibodies bind to a MICB protein that is membrane-bound MICB protein. In some embodiments, the antibodies bind to a MICB protein that is soluble MICB protein. In some embodiments, the antibodies bind to a MICB protein that is both membrane-bound MICB protein and soluble MICB protein.

In some embodiments, antibodies that specifically bind to MICA/B are monoclonal antibodies. In some embodiments, the antibody is an antigen binding fragment. In some embodiments, the antibody is selected from a whole immunoglobulin, an scFv, a Fab, a F(ab')2, or a disulfide linked Fv. In some embodiments, the antibody is an IgG or an IgM. In some embodiments, the antibody is humanized. In some embodiments, the antibody is chimeric.

MICA/B Antibody Heavy and Light Chain

Disclosed herein are antibodies that specifically bind to MICA/B having a light chain. In some embodiments, antibodies binding to MICA/B comprise a light chain having an amino acid sequence at least about 70% identical to an amino acid sequence set forth as SEQ ID NO: 21, SEQ ID NO: 23, or SEQ ID NO: 24. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO:21, SEQ ID NO: 23, or SEQ ID NO: 24. In some embodiments, the light chain has an amino acid sequence 100% identical to an amino acid sequence set forth as SEQ ID NO: 21, SEQ ID NO: 23, or SEQ ID NO: 24.

Further disclosed herein are antibodies that specifically bind to MICA/B having a heavy chain. In some embodiments, antibodies binding to MICA/B comprise a heavy chain having an amino acid sequence at least about 70% identical to an amino acid sequence set forth as SEQ ID NO: 22, SEQ ID NO: 25, or SEQ ID NO: 26. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22, SEQ ID NO: 25, or SEQ ID NO: 26. In some embodiments, the heavy chain has an amino acid sequence 100% identical to an amino acid sequence set forth as SEQ ID NO: 22, SEQ ID NO: 25, or SEQ ID NO: 26.

Also disclosed herein are antibodies binding to MICAS comprising a light chain and a heavy chain. In some embodiments, antibodies binding to MICA/B comprise a light chain having an amino acid sequence at least about 70% identical to an amino acid sequence set forth as SEQ ID NO: 21, SEQ ID NO: 23, or SEQ ID NO: 24 and a heavy chain having an amino acid sequence at least about 70% identical to an amino acid sequence set forth as SEQ ID NO: 22, SEQ ID NO: 25, or SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21, SEQ ID NO: 23, or SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22, SEQ ID NO: 25, or SEQ ID NO: 26. In some embodiments, the light chain has an amino acid sequence 100% identical to an amino acid sequence set forth as SEQ ID NO: 21, SEQ ID NO: 23, or SEQ ID NO: 24 and the heavy chain has an amino acid sequence 100% identical to an amino acid sequence set forth as SEQ ID NO: 22, SEQ ID NO: 25, or SEQ ID NO: 26.

In some embodiments, antibodies binding to MICA/B comprise a light chain having an amino acid sequence at least about 70% identical to an amino acid sequence set forth as SEQ ID NO: 21 and a heavy chain having an amino acid sequence at least about 70% identical to an amino acid sequence set forth as SEQ ID NO: 22. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22. In some embodiments, the light chain has an amino acid sequence 100% identical to an amino acid sequence set forth as SEQ ID NO: 21 and the heavy chain has an amino acid sequence 100% identical to an amino acid sequence set forth as SEQ ID NO: 22.

In some embodiments, antibodies binding to MICA/B comprise a light chain having an amino acid sequence at least about 70% identical to an amino acid sequence set forth as SEQ ID NO: 23 and a heavy chain having an amino acid sequence at least about 70% identical to an amino acid sequence set forth as SEQ ID NO: 25. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 23 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 25. In some embodiments, the light chain has an amino acid sequence 100% identical to an amino acid sequence set forth as SEQ ID NO: 23 and the heavy chain has an amino acid sequence 100% identical to an amino acid sequence set forth as SEQ ID NO: 25.

In some embodiments, antibodies binding to MICA/B comprise a light chain having an amino acid sequence at least about 70% identical to an amino acid sequence set forth as SEQ ID NO: 23 and a heavy chain having an amino acid sequence at least about 70% identical to an amino acid sequence set forth as SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 23 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 26. In some embodiments, the light chain has an amino acid sequence 100% identical to an amino acid sequence set forth as SEQ ID NO: 23 and the heavy chain has an amino acid sequence 100% identical to an amino acid sequence set forth as SEQ ID NO: 26.

In some embodiments, antibodies binding to MICA/B comprise a light chain having an amino acid sequence at least about 70% identical to an amino acid sequence set forth as SEQ ID NO: 24 and a heavy chain having an amino acid sequence at least about 70% identical to an amino acid sequence set forth as SEQ ID NO: 25. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 25. In some embodiments, the light chain has an amino acid sequence 100% identical to an amino acid sequence set forth as SEQ ID NO: 24 and the heavy chain has an amino acid sequence 100% identical to an amino acid sequence set forth as SEQ ID NO: 25.

In some embodiments, antibodies binding to MICA/B comprise a light chain having an amino acid sequence at least about 70% identical to an amino acid sequence set forth as SEQ ID NO: 24 and a heavy chain having an amino acid sequence at least about 70% identical to an amino acid sequence set forth as SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 26. In some embodiments, the light chain has an amino acid sequence 100% identical to an amino acid sequence set forth as SEQ ID NO: 24 and the heavy chain has an amino acid sequence 100% identical to an amino acid sequence set forth as SEQ ID NO: 26.

MICA/B Antibody Variable Domain

Disclosed herein are antibodies that specifically bind to MICA/B having a light chain comprising a light chain variable domain (VL). In some embodiments, antibodies binding to MICA/B comprise a light chain variable domain (VL) having an amino acid sequence at least about 70% identical to an amino acid sequence set forth as SEQ ID NO: 7, SEQ ID NO: 15, or SEQ ID NO: 19. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7, SEQ ID NO: 15, or SEQ ID NO: 19. In some embodiments, the VL has an amino acid sequence 100% identical to an amino acid sequence set forth as SEQ ID NO: 7, SEQ ID NO: 15, or SEQ ID NO: 19.

Further disclosed herein are antibodies that specifically bind to MICA/B having a heavy chain comprising a heavy chain variable domain (VH). In some embodiments, antibodies binding to MICA/B comprise a heavy chain variable domain (VH) having an amino acid sequence at least about 70% identical to an amino acid sequence set forth as SEQ ID NO: 8, SEQ ID NO: 16, or SEQ ID NO: 20. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8, SEQ ID NO: 16, or SEQ ID NO: 20. In some embodiments, the VH has an amino acid sequence 100% identical to an amino acid sequence set forth as SEQ ID NO: 8, SEQ ID NO: 16, or SEQ ID NO: 20.

Also disclosed herein are antibodies binding to MICA/B comprising a light chain variable domain (VL) and a heavy chain variable domain (VH). In some embodiments, antibodies binding to MICA/B comprise a light chain variable domain (VL) having an amino acid sequence at least about 70% identical to an amino acid sequence set forth as SEQ ID NO: 7, SEQ ID NO: 15, or SEQ ID NO: 19 and a heavy chain variable domain (VH) having an amino acid sequence at least about 70% identical to an amino acid sequence set forth as SEQ ID NO: 8, SEQ ID NO: 16, or SEQ ID NO: 20. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7, SEQ ID NO: 15, or SEQ ID NO: 19 and the VH has an amino acid sequence at least about 75%, 80%, 81%, 82%, 83%, 84% 85%, 86%, 87%, 88%, 89%, 90%, 91%, 92%, 93%, 94%, 95%, 96%, 97%, 98%, or 99% identical to an amino acid sequence set forth as SEQ ID NO: 8, SEQ ID NO: 16, or SEQ ID NO: 20. In some embodiments, the VL has an amino acid sequence 100% identical to an amino acid sequence set forth as SEQ ID NO: 7, SEQ ID NO: 15, or SEQ ID NO: 19 and the VH has an amino acid sequence 100% identical to an amino acid sequence set forth as SEQ ID NO: 8, SEQ ID NO: 16, or SEQ ID NO: 20.

In some embodiments, antibodies binding to MICA/B comprise a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

In some embodiments, antibodies binding to MICA/B comprise a light chain variable domain (VL) having an amino acid sequence at least about 70% identical to an amino acid sequence set forth as SEQ ID NO: 15 and a heavy chain variable domain (VH) having an amino acid sequence at least about 70% identical to an amino acid sequence set forth as SEQ ID NO: 16. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16. In some embodiments, the VL has an amino acid sequence 100% identical to an amino acid sequence set forth as SEQ ID NO: 15 and the VH has an amino acid sequence 100% identical to an amino acid sequence set forth as SEQ ID NO: 16.

In some embodiments, antibodies binding to MICA/B comprise a light chain variable domain (VL) having an amino acid sequence at least about 70% identical to an amino acid sequence set forth as SEQ ID NO: 19 and a heavy chain variable domain (VH) having an amino acid sequence at least about 70% identical to an amino acid sequence set forth as SEQ ID NO: 20. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 19 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 20. In some embodiments, the VL has an amino acid sequence 100% identical to an amino acid sequence set forth as SEQ ID NO: 19 and the VH has an amino acid sequence 100% identical to an amino acid sequence set forth as SEQ ID NO: 20.

MICA/B Antibody Complementarity Determining Regions

Disclosed herein are antibodies that specifically bind to MICA/B having a light chain comprising a light chain complementarity determining region (CDR). In some embodiments, antibodies binding to MICA/B comprise a light chain CDR sequence having an amino acid sequence at least about 70% identical to at least one of the amino acid sequences set forth as SEQ ID NOS: 1-3, 9-11, and 17. In some embodiments, antibodies binding to MICA/B comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3, 9-11, and 17. In some embodiments, antibodies binding to MICA/B comprise a light chain CDR sequence having an amino acid sequence 100% identical to at least one of the amino acid sequences set forth as SEQ ID NOS: 1-3, 9-11, and 17.

Further disclosed herein are antibodies that specifically bind to MICA/B having a heavy chain comprising a heavy chain complementarity determining region (CDR). In some embodiments, antibodies binding to MICA/B comprise a heavy chain CDR sequence having an amino acid sequence at least about 70% identical to at least one of the amino acid sequences set forth as SEQ ID NOS: 4-6, 12-14, and 18. In some embodiments, antibodies binding to MICA/B comprise a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6, 12-14, and 18. In some embodiments, antibodies binding to MICA/B comprise a heavy chain CDR sequence having an amino acid sequence 100% identical to at least one of the amino acid sequences set forth as SEQ ID NOS: 4-6, 12-14, and 18.

Also disclosed herein are antibodies binding to MICA/B comprising a light chain complementarity determining region (CDR) and a heavy chain complementarity determining region (CDR). In some embodiments, antibodies binding to MICA/B comprise a light chain CDR sequence having an amino acid sequence at least about 70% identical to at least one of the amino acid sequences set forth as SEQ ID NOS: 1-3, 9-11, and 17 and a heavy chain CDR sequence having an amino acid sequence at least about 70% identical to at least one of the amino acid sequences set forth as SEQ ID NOS: 4-6, 12-14, and 18. In some embodiments, antibodies binding to MICA/B comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3, 9-11, and 17 and a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6, 12-14, and 18. In some embodiments, antibodies binding to MICA/B comprise a light chain CDR sequence having an amino acid sequence 100% identical to at least one of the amino acid sequences set forth as SEQ ID NOS: 1-3, 9-11, and 17 and a heavy chain CDR sequence having an amino acid sequence at least about 100% identical to at least one of the amino acid sequences set forth as SEQ ID NOS: 4-6, 12-14, and 18.

In some embodiments, antibodies binding to MICA/B comprise a light chain complementarity determining region 1 (CDR1) having an amino acid sequence at least about 70% identical to one of SEQ ID NO: 1, SEQ ID NO: 9, or SEQ ID NO: 17, a light chain complementarity determining region 2 (CDR2) having an amino acid sequence at least about 70% identical to one of SEQ ID NOS: SEQ ID NO: 2, or SEQ ID NO: 10, a light chain complementarity determining region 3 (CDR3) having an amino acid sequence at least about 70% identical to one of SEQ ID NO: 3, or SEQ ID NO: 11, a heavy chain complementarity determining region 1 (CDR1) having an amino acid sequence at least about 70% identical to one of SEQ ID NO: 4, or SEQ ID NO: 12, a heavy chain complementarity determining region 2 (CDR2) having an amino acid sequence at least about 70% identical to one of SEQ ID NO: 5, SEQ ID NO: 13, or SEQ ID NO: 18, and a heavy chain complementarity determining region 3 (CDR3) having an amino acid sequence at least about 70% identical to one of SEQ ID NO: 6, or SEQ ID NO: 14. In some embodiments, antibodies binding to MICA/B comprise a light chain complementarity determining region 1 (CDR1) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 1, SEQ ID NO: 9, or SEQ ID NO: 17, a light chain complementarity determining region 2 (CDR2) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NOS: SEQ ID NO: 2, or SEQ ID NO: 10, a light chain complementarity determining region 3 (CDR3) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 3, or SEQ ID NO: 11, a heavy chain complementarity determining region 1 (CDR1) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 4, or SEQ ID NO: 12, a heavy chain complementarity determining region 2 (CDR2) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 5, SEQ ID NO: 13, or SEQ ID NO: 18, and a heavy chain complementarity determining region 3 (CDR3) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 6, or SEQ ID NO: 14. In some embodiments, antibodies binding to MICA/B comprise a light chain complementarity determining region 1 (CDR1) having an amino acid sequence 100% identical to one of SEQ ID NO: 1, SEQ ID NO: 9, or SEQ ID NO: 17, a light chain complementarity determining region 2 (CDR2) having an amino acid sequence 100% identical to one of SEQ ID NOS: SEQ ID NO: 2, or SEQ ID NO: 10, a light chain complementarity determining region 3 (CDR3) having an amino acid sequence 100% identical to one of SEQ ID NO: 3, or SEQ ID NO: 11, a heavy chain complementarity determining region 1 (CDR1) having an amino acid sequence 100% identical to one of SEQ ID NO: 4, or SEQ ID NO: 12, a heavy chain complementarity determining region 2 (CDR2) having an amino acid sequence 100% identical to one of SEQ ID NO: 5, SEQ ID NO: 13, or SEQ ID NO: 18, and a heavy chain complementarity determining region 3 (CDR3) having an amino acid sequence 100% identical to one of SEQ ID NO: 6, or SEQ ID NO: 14.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies binding to MICA/B comprise at least one of a light chain CDR1 having an amino acid sequence at least about 70% identical to an amino acid sequence set forth as SEQ ID NO: 9, a light chain CDR2 having an amino acid sequence at least about 70% identical to an amino acid sequence set forth as SEQ ID NO: 10, and a light chain CDR3 having an amino acid sequence at least about 70% identical to an amino acid sequence set forth as SEQ ID NO: 11. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11. In some embodiments, antibodies binding to MICA/B comprise at least one of a light chain CDR1 having an amino acid sequence 100% identical to an amino acid sequence set forth as SEQ ID NO: 9, a light chain CDR2 having an amino acid sequence 100% identical to an amino acid sequence set forth as SEQ ID NO: 10, and a light chain CDR3 having an amino acid sequence 100% identical to an amino acid sequence set forth as SEQ ID NO: 11.

In some embodiments, antibodies binding to MICA/B comprise at least one of a light chain CDR1 having an amino acid sequence at least about 70% identical to an amino acid sequence set forth as SEQ ID NO: 17, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 17, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 17, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

In some embodiments, antibodies binding to MICA/B comprise at least one of a heavy chain CDR1 having an amino acid sequence at least about 70% identical to an amino acid sequence set forth as SEQ ID NO: 12, a heavy chain CDR2 having an amino acid sequence at least about 70% identical to an amino acid sequence set forth as SEQ ID NO: 13, a heavy chain CDR3 having an amino acid sequence at least about 70% identical to an amino acid sequence set forth as SEQ ID NO: 14. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, antibodies binding to MICA/B comprise at least one of a heavy chain CDR1 having an amino acid sequence 100% identical to an amino acid sequence set forth as SEQ ID NO: 12, a heavy chain CDR2 having an amino acid sequence 100% identical to an amino acid sequence set forth as SEQ ID NO: 13, a heavy chain CDR3 having an amino acid sequence 100% identical to an amino acid sequence set forth as SEQ ID NO: 14.

In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 18, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 18, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 18, a heavy chain CDR3 having an amino acid sequence 100% identical to an amino acid sequence set forth as SEQ ID NO: 6.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO:3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA5 comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

In some embodiments, antibodies binding to MICA/B comprise at least one of a light chain CDR1 having an amino acid sequence at least about 70% identical to an amino acid sequence set forth as SEQ ID NO: 9, a light chain CDR2 having an amino acid sequence at least about 70% identical to an amino acid sequence set forth as SEQ ID NO: 10, a light chain CDR3 having an amino acid sequence at least about 70% identical to an amino acid sequence set forth as SEQ ID NO: 11, a heavy chain CDR1 having an amino acid sequence at least about 70% identical to an amino acid sequence set forth as SEQ ID NO: 12, a heavy chain CDR2 having an amino acid sequence at least about 70% identical to an amino acid sequence set forth as SEQ ID NO: 13, and a heavy chain CDR3 having an amino acid sequence at least about 70% identical to an amino acid sequence set forth as SEQ ID NO: 14. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, antibodies binding to MICA/B comprise at least one of a light chain CDR1 having an amino acid sequence 100% identical to an amino acid sequence set forth as SEQ ID NO: 9, a light chain CDR2 having an amino acid sequence 100% identical to an amino acid sequence set forth as SEQ ID NO: 10, a light chain CDR3 having an amino acid sequence 100% identical to an amino acid sequence set forth as SEQ ID NO: 11, a heavy chain CDR1 having an amino acid sequence 100% identical to an amino acid sequence set forth as SEQ ID NO: 12, a heavy chain CDR2 having an amino acid sequence 100% identical to an amino acid sequence set forth as SEQ ID NO: 13, and a heavy chain CDR3 having an amino acid sequence 100% identical to an amino acid sequence set forth as SEQ ID NO: 14.

In some embodiments, antibodies binding to MICA/B comprise at least one of a light chain CDR1 having an amino acid sequence at least about 70% identical to an amino acid sequence set forth as SEQ ID NO: 17, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 18, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 17, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 18, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 17, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 18, and a heavy chain CDR3 having an amino acid sequence 100% identical to an amino acid sequence set forth as SEQ ID NO: 6.

In some embodiments, antibodies binding to MICA/B do not have at least one CDR selected from the list comprising: SEQ ID NO: 29, SEQ ID NO: 30, SEQ ID NO: 31, SEQ ID NO: 32, SEQ ID NO: 33, and SEQ ID NO: 34.

Competitive Binding

Disclosed herein, in some embodiments, are antibodies that competitively bind to MICA/B with an antibody comprising a light chain variable domain (VL) having an amino acid sequence at least about 70% identical to an amino acid sequence set forth as SEQ ID NO: 27. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 27. In some embodiments, the VL has an amino acid sequence 100% identical to an amino acid sequence set forth as SEQ ID NO: 27.

Disclosed herein, in some embodiments, are antibodies that competitively bind to MICA/B with an antibody comprising a heavy chain variable domain (VH) having an amino acid sequence at least about 70% identical to an amino acid sequence set forth as SEQ ID NO: 28. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 28. In some embodiments, the VH has an amino acid sequence 100% identical to an amino acid sequence set forth as SEQ ID NO: 28.

Disclosed herein, in some embodiments, are antibodies that competitively bind to MICA/B with an antibody comprising a light chain variable domain (VL) having an amino acid sequence at least about 70% identical to an amino acid sequence set forth as SEQ ID NO: 27 and a heavy chain variable domain (VH) having an amino acid sequence at least about 70% identical to an amino acid sequence set forth as SEQ ID NO: 28. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 27 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 28. In some embodiments, the VL has an amino acid sequence 100% identical to an amino acid sequence set forth as SEQ ID NO: 27 and the VH has an amino acid sequence 100% identical to an amino acid sequence set forth as SEQ ID NO: 28.

Methods of Treatment and Use

Provided herein are methods of treating cancer (e.g. hepatocellular carcinoma) in an individual in need thereof comprising administration of an anti-MICA/B antibody disclosed herein.

Further provided herein are methods of reducing level of soluble MICA/B proteins in an individual in need thereof comprising administration of an anti-MICA/B antibody disclosed herein.

Also provided herein are methods of alleviating or inhibiting the immunosuppressive environment by preventing or blocking the interaction between soluble MICA/B and NKG2D receptors in an individual in need thereof comprising administration of an anti-MICA/B antibody disclosed herein.

In some embodiments, antibodies binding to MICA/B comprise a light chain CDR sequence having an amino acid sequence at least about 70% identical to at least one of the amino acid sequences set forth as SEQ ID NOS: 1-3, 9-11, and 17. In some embodiments, antibodies binding to MICA/B comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3, 9-11, and 17. In some embodiments, antibodies binding to MICA/B comprise a light chain CDR sequence having an amino acid sequence 100% identical to at least one of the amino acid sequences set forth as SEQ ID NOS: 1-3, 9-11, and 17.

In some embodiments, antibodies binding to MICA/B comprise a heavy chain CDR sequence having an amino acid sequence at least about 70% identical to at least one of the amino acid sequences set forth as SEQ ID NOS: 4-6, 12-14, and 18. In some embodiments, antibodies binding to MICA/B comprise a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6, 12-14, and 18. In some embodiments, antibodies binding to MICA/B comprise a heavy chain CDR sequence having an amino acid sequence 100% identical to at least one of the amino acid sequences set forth as SEQ ID NOS: 4-6, 12-14, and 18.

In some embodiments, antibodies binding to MICA/B comprise a light chain CDR sequence having an amino acid sequence at least about 70% identical to at least one of the amino acid sequences set forth as SEQ ID NOS: 1-3, 9-11, and 17 and a heavy chain CDR sequence having an amino acid sequence at least about 70% identical to at least one of the amino acid sequences set forth as SEQ ID NOS: 4-6, 12-14, and 18. In some embodiments, antibodies binding to MICA/B comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3, 9-11, and 17 and a heavy chain CDR sequence having an amino acid sequence at least 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6, 12-14, and 18. In some embodiments, antibodies binding to MICA/B comprise a light chain CDR sequence having an amino acid sequence 100% identical to at least one of the amino acid sequences set forth as SEQ ID NOS: 1-3, 9-11, and 17 and a heavy chain CDR sequence having an amino acid sequence at least about 100% identical to at least one of the amino acid sequences set forth as SEQ ID NOS: 4-6, 12-14, and 18.

In some embodiments, antibodies binding to MICA/B comprise a light chain complementarity determining region 1 (CDR1) having an amino acid sequence at least about 70% identical to one of SEQ ID NO: 1, SEQ ID NO: 9, or SEQ ID NO: 17, a light chain complementarity determining region 2 (CDR2) having an amino acid sequence at least about 70% identical to one of SEQ ID NOS: SEQ ID NO: 2, or SEQ ID NO: 10, a light chain complementarity determining region 3 (CDR3) having an amino acid sequence at least about 70% identical to one of SEQ ID NO: 3, or SEQ ID NO: 11, a heavy chain complementarity determining region 1 (CDR1) having an amino acid sequence at least about 70% identical to one of SEQ ID NO: 4, or SEQ ID NO: 12, a heavy chain complementarity determining region 2 (CDR2) having an amino acid sequence at least about 70% identical to one of SEQ ID NO: 5, SEQ ID NO: 13, or SEQ ID NO: 18, and a heavy chain complementarity determining region 3 (CDR3) having an amino acid sequence at least about 70% identical to one of SEQ ID NO: 6, or SEQ ID NO: 14. In some embodiments, antibodies binding to MICA/B comprise a light chain complementarity determining region 1 (CDR1) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 1, SEQ ID NO: 9, or SEQ ID NO: 17, a light chain complementarity determining region 2 (CDR2) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NOS: SEQ ID NO: 2, or SEQ ID NO: 10, a light chain complementarity determining region 3 (CDR3) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 3, or SEQ ID NO: 11, a heavy chain complementarity determining region 1 (CDR1) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 4, or SEQ ID NO: 12, a heavy chain complementarity determining region 2 (CDR2) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 5, SEQ ID NO: 13, or SEQ ID NO: 18, and a heavy chain complementarity determining region 3 (CDR3) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 6, or SEQ ID NO: 14. In some embodiments, antibodies binding to MICA/B comprise a light chain complementarity determining region 1 (CDR1) having an amino acid sequence 100% identical to one of SEQ ID NO: 1, SEQ ID NO: 9, or SEQ ID NO: 17, a light chain complementarity determining region 2 (CDR2) having an amino acid sequence 100% identical to one of SEQ ID NOS: SEQ ID NO: 2, or SEQ ID NO: 10, a light chain complementarity determining region 3 (CDR3) having an amino acid sequence 100% identical to one of SEQ ID NO: 3, or SEQ ID NO: 11, a heavy chain complementarity determining region 1 (CDR1) having an amino acid sequence 100% identical to one of SEQ ID NO: 4, or SEQ ID NO: 12, a heavy chain complementarity determining region 2 (CDR2) having an amino acid sequence 100% identical to one of SEQ ID NO: 5, SEQ ID NO: 13, or SEQ ID NO: 18, and a heavy chain complementarity determining region 3 (CDR3) having an amino acid sequence 100% identical to one of SEQ ID NO: 6, or SEQ ID NO: 14.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies binding to MICA/B comprise at least one of a light chain CDR1 having an amino acid sequence at least about 70% identical to an amino acid sequence set forth as SEQ ID NO: 9, a light chain CDR2 having an amino acid sequence at least about 70% identical to an amino acid sequence set forth as SEQ ID NO: 10, and a light chain CDR3 having an amino acid sequence at least about 70% identical to an amino acid sequence set forth as SEQ ID NO: 11. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11. In some embodiments, antibodies binding to MICA/B comprise at least one of a light chain CDR1 having an amino acid sequence 100% identical to an amino acid sequence set forth as SEQ ID NO: 9, a light chain CDR2 having an amino acid sequence 100% identical to an amino acid sequence set forth as SEQ ID NO: 10, and a light chain CDR3 having an amino acid sequence 100% identical to an amino acid sequence set forth as SEQ ID NO: 11

In some embodiments, antibodies binding to MICA/B comprise at least one of a light chain CDR1 having an amino acid sequence at least about 70% identical to an amino acid sequence set forth as SEQ ID NO: 17, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 17, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 17, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

In some embodiments, antibodies binding to MICA/B comprise at least one of a heavy chain CDR1 having an amino acid sequence at least about 70% identical to an amino acid sequence set forth as SEQ ID NO: 12, a heavy chain CDR2 having an amino acid sequence at least about 70% identical to an amino acid sequence set forth as SEQ ID NO: 13, a heavy chain CDR3 having an amino acid sequence at least about 70% identical to an amino acid sequence set forth as SEQ ID NO: 14. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, antibodies binding to MICA/B comprise at least one of a heavy chain CDR1 having an amino acid sequence 100% identical to an amino acid sequence set forth as SEQ ID NO: 12, a heavy chain CDR2 having an amino acid sequence 100% identical to an amino acid sequence set forth as SEQ ID NO: 13, a heavy chain CDR3 having an amino acid sequence 100% identical to an amino acid sequence set forth as SEQ ID NO: 14.

In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 18, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 18, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 18, a heavy chain CDR3 having an amino acid sequence 100% identical to an amino acid sequence set forth as SEQ ID NO: 6.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

In some embodiments, antibodies binding to MICA/B comprise at least one of a light chain CDR1 having an amino acid sequence at least about 70% identical to an amino acid sequence set forth as SEQ ID NO: 9, a light chain CDR2 having an amino acid sequence at least about 70% identical to an amino acid sequence set forth as SEQ ID NO: 10, a light chain CDR3 having an amino acid sequence at least about 70% identical to an amino acid sequence set forth as SEQ ID NO: 11, a heavy chain CDR1 having an amino acid sequence at least about 70% identical to an amino acid sequence set forth as SEQ ID NO: 12, a heavy chain CDR2 having an amino acid sequence at least about 70% identical to an amino acid sequence set forth as SEQ ID NO: 13, and a heavy chain CDR3 having an amino acid sequence at least about 70% identical to an amino acid sequence set forth as SEQ ID NO: 14. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, antibodies binding to MICA/B comprise at least one of a light chain CDR1 having an amino acid sequence 100% identical to an amino acid sequence set forth as SEQ ID NO: 9, a light chain CDR2 having an amino acid sequence 100% identical to an amino acid sequence set forth as SEQ ID NO: 10, a light chain CDR3 having an amino acid sequence 100% identical to an amino acid sequence set forth as SEQ ID NO: 11, a heavy chain CDR1 having an amino acid sequence 100% identical to an amino acid sequence set forth as SEQ ID NO: 12, a heavy chain CDR2 having an amino acid sequence 100% identical to an amino acid sequence set forth as SEQ ID NO: 13, and a heavy chain CDR3 having an amino acid sequence 100% identical to an amino acid sequence set forth as SEQ ID NO: 14.

In some embodiments, antibodies binding to MICA/B comprise at least one of a light chain CDR1 having an amino acid sequence at least about 70% identical to an amino acid sequence set forth as SEQ ID NO: 17, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 18, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 17, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO:3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% Identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 18, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 17, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 18, and a heavy chain CDR3 having an amino acid sequence 100% identical to an amino acid sequence set forth as SEQ ID NO: 6.

In some embodiments, antibodies binding to MICA/B do not have at least one CDR selected from the list comprising: SEQ ID NO: 29, SEQ ID NO: 30, SEQ ID NO: 31, SEQ ID NO: 32, SEQ ID NO: 33, and SEQ ID NO: 34.

In some embodiments, antibodies binding to MICA/B comprise a light chain variable domain (VL) having an amino acid sequence at least about 70% identical to an amino acid sequence set forth as SEQ ID NO: 7, SEQ ID NO: 15, or SEQ ID NO: 19. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7, SEQ ID NO: 15, or SEQ ID NO: 19. In some embodiments, the VL has an amino acid sequence 100% identical to an amino acid sequence set forth as SEQ ID NO: 7, SEQ ID NO: 15, or SEQ ID NO: 19.

In some embodiments, antibodies binding to MICA/B comprise a heavy chain variable domain (VH) having an amino acid sequence at least about 70% identical to an amino acid sequence set forth as SEQ ID NO: 8, SEQ ID NO: 16, or SEQ ID NO: 20. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8, SEQ ID NO: 16, or SEQ ID NO: 20. In some embodiments, the VH has an amino acid sequence 100% identical to an amino acid sequence set forth as SEQ ID NO: 8, SEQ ID NO: 16, or SEQ ID NO: 20.

In some embodiments, antibodies binding to MICA/B comprise a light chain variable domain (VL) having an amino acid sequence at least about 70% identical to an amino acid sequence set forth as SEQ ID NO: 7, SEQ ID NO: 15, or SEQ ID NO: 19 and a heavy chain variable domain (VH) having an amino acid sequence at least about 70% identical to an amino acid sequence set forth as SEQ ID NO: 8, SEQ ID NO: 16, or SEQ ID NO: 20. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7, SEQ ID NO: 15, or SEQ ID NO: 19 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8, SEQ ID NO: 16, or SEQ ID NO: 20. In some embodiments, the VL has an amino acid sequence 100% identical to an amino acid sequence set forth as SEQ ID NO: 7, SEQ ID NO: 15, or SEQ ID NO: 19 and the VH has an amino acid sequence 100% identical to an amino acid sequence set forth as SEQ ID NO: 8, SEQ ID NO: 16, or SEQ ID NO: 20.

In some embodiments, antibodies binding to MICA/B comprise a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

In some embodiments, antibodies binding to MICA/B comprise a light chain variable domain (VL) having an amino acid sequence at least about 70% identical to an amino acid sequence set forth as SEQ ID NO: 15 and a heavy chain variable domain (VH) having an amino acid sequence at least about 70% identical to an amino acid sequence set forth as SEQ ID NO: 16. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16. In some embodiments, the VL has an amino acid sequence 100% identical to an amino acid sequence set forth as SEQ ID NO: 15 and the VH has an amino acid sequence 100% identical to an amino acid sequence set forth as SEQ ID NO: 16.

In some embodiments, antibodies binding to MICA/B comprise a light chain variable domain (VL) having an amino acid sequence at least about 70% identical to an amino acid sequence set forth as SEQ ID NO: 19 and a heavy chain variable domain (VH) having an amino acid sequence at least about 70% identical to an amino acid sequence set forth as SEQ ID NO: 20. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 19 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 20. In some embodiments, the VL has an amino acid sequence 100% identical to an amino acid sequence set forth as SEQ ID NO: 19 and the VH has an amino acid sequence 100% identical to an amino acid sequence set forth as SEQ ID NO: 20.

In some embodiments, antibodies binding to MICA/B comprise a light chain having an amino acid sequence at least about 70% identical to an amino acid sequence set forth as SEQ ID NO: 21, SEQ ID NO: 23, or SEQ ID NO: 24. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21, SEQ ID NO: 23, or SEQ ID NO: 24. In some embodiments, the light chain has an amino acid sequence 100% identical to an amino acid sequence set forth as SEQ ID NO: 21, SEQ ID NO: 23, or SEQ ID NO: 24.

In some embodiments, antibodies binding to MICA/B comprise a heavy chain having an amino acid sequence at least about 70% identical to an amino acid sequence set forth as SEQ ID NO: 22, SEQ ID NO: 25, or SEQ ID NO: 26. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22, SEQ ID NO: 25, or SEQ ID NO: 26. In some embodiments, the heavy chain has an amino acid sequence 100% identical to an amino acid sequence set forth as SEQ ID NO: 22, SEQ ID NO: 25, or SEQ ID NO: 26.

Also disclosed herein are antibodies binding to MICA/B comprising a light chain and a heavy chain. In some embodiments, antibodies binding to MICA/B comprise a light chain having an amino acid sequence at least about 70% identical to an amino acid sequence set forth as SEQ ID NO: 21, SEQ ID NO: 23, or SEQ ID NO: 24 and a heavy chain having an amino acid sequence at least about 70% identical to an amino acid sequence set forth as SEQ ID NO: 22, SEQ ID NO: 25, or SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21, SEQ ID NO: 23, or SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22, SEQ ID NO: 25, or SEQ ID NO: 26. In some embodiments, the light chain has an amino acid sequence 100% identical to an amino acid sequence set forth as SEQ ID NO: 21, SEQ ID NO: 23, or SEQ ID NO: 24 and the heavy chain has an amino acid sequence 100% identical to an amino acid sequence set forth as SEQ ID NO: 22, SEQ ID NO: 25, or SEQ ID NO: 26.

In some embodiments, antibodies binding to MICA/B comprise a light chain having an amino acid sequence at least about 70% identical to an amino acid sequence set forth as SEQ ID NO: 21 and a heavy chain having an amino acid sequence at least about 70% identical to an amino acid sequence set forth as SEQ ID NO: 22. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22. In some embodiments, the light chain has an amino acid sequence 100% identical to an amino acid sequence set forth as SEQ ID NO: 21 and the heavy chain has an amino acid sequence 100% identical to an amino acid sequence set forth as SEQ ID NO: 22.

In some embodiments, antibodies binding to MICA/B comprise a light chain having an amino acid sequence at least about 70% identical to an amino acid sequence set forth as SEQ ID NO: 23 and a heavy chain having an amino acid sequence at least about 70% identical to an amino acid sequence set forth as SEQ ID NO: 25. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 23 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 25. In some embodiments, the light chain has an amino acid sequence 100% identical to an amino acid sequence set forth as SEQ ID NO: 23 and the heavy chain has an amino acid sequence 100% identical to an amino acid sequence set forth as SEQ ID NO: 25.

In some embodiments, antibodies binding to MICA/B comprise a light chain having an amino acid sequence at least about 70% identical to an amino acid sequence set forth as SEQ ID NO: 23 and a heavy chain having an amino acid sequence at least about 70% identical to an amino acid sequence set forth as SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 23 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 26. In some embodiments, the light chain has an amino acid sequence 100% identical to an amino acid sequence set forth as SEQ ID NO: 23 and the heavy chain has an amino acid sequence 100% identical to an amino acid sequence set forth as SEQ ID NO: 26.

In some embodiments, antibodies binding to MICA/B comprise a light chain having an amino acid sequence at least about 70% identical to an amino acid sequence set forth as SEQ ID NO: 24 and a heavy chain having an amino acid sequence at least about 70% identical to an amino acid sequence set forth as SEQ ID NO: 25. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 25. In some embodiments, the light chain has an amino acid sequence 100% identical to an amino acid sequence set forth as SEQ ID NO: 24 and the heavy chain has an amino acid sequence 100% identical to an amino acid sequence set forth as SEQ ID NO: 25.

In some embodiments, antibodies binding to MICA/B comprise a light chain having an amino acid sequence at least about 70% identical to an amino acid sequence set forth as SEQ ID NO: 24 and a heavy chain having an amino acid sequence at least about 70% identical to an amino acid sequence set forth as SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 26. In some embodiments, the light chain has an amino acid sequence 100% identical to an amino acid sequence set forth as SEQ ID NO: 24 and the heavy chain has an amino acid sequence 100% identical to an amino acid sequence set forth as SEQ ID NO: 26.

In some embodiments, antibodies competitively bind to MICA/B with an antibody comprising a light chain variable domain (VL) having an amino acid sequence at least about 70% identical to an amino acid sequence set forth as SEQ ID NO: 27. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 27. In some embodiments, the VL has an amino acid sequence 100% identical to an amino acid sequence set forth as SEQ ID NO: 27.

In some embodiments, antibodies competitively bind to MICA/B with an antibody comprising a heavy chain variable domain (VH) having an amino acid sequence at least about 70% identical to an amino acid sequence set forth as SEQ ID NO: 28. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 28. In some embodiments, the VH has an amino acid sequence 100% identical to an amino acid sequence set forth as SEQ ID NO: 28.

In some embodiments, antibodies competitively bind to MICA/B with an antibody comprising a light chain variable domain (VL) having an amino acid sequence at least about 70% identical to an amino acid sequence set forth as SEQ ID NO: 27 and a heavy chain variable domain (VH) having an amino acid sequence at least about 70% identical to an amino acid sequence set forth as SEQ ID NO: 28. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 27 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 28. In some embodiments, the VL has an amino acid sequence 100% identical to an amino acid sequence set forth as SEQ ID NO: 27 and the VH has an amino acid sequence 100% identical to an amino acid sequence set forth as SEQ ID NO: 28.

In some embodiments, the antibodies specifically bind to a MICA protein. In some embodiments, the antibodies specifically bind to a MICB protein. In some embodiments, the antibodies specifically bind to both MICA and MICB protein. In some embodiments, the antibodies bind to an alpha-3 domain of a MICA protein. In some embodiments, the antibodies bind to an alpha-3 domain of a MICB protein. In some embodiments, the antibodies bind to an alpha-3 domain of both MICA and MICB protein. In some embodiments, the antibodies bind to a MICA protein that is membrane-bound MICA protein. In some embodiments, the antibodies bind to a MICA protein that is soluble MICA protein. In some embodiments, the antibodies bind to a MICA protein that is both membrane-bound MICA protein and soluble MICA protein. In some embodiments, the antibodies bind to a MICB protein that is membrane-bound MICB protein. In some embodiments, the antibodies bind to a MICB protein that is soluble MICB protein. In some embodiments, the antibodies bind to a MICB protein that is both membrane-bound MICB protein and soluble MICB protein.

In some embodiments, antibodies that specifically bind to MICA/B are monoclonal antibodies. In some embodiments, the antibody is an antigen binding fragment. In some embodiments, the antibody is selected from a whole immunoglobulin, an scFv, a Fab, a F(ab')2, or a disulfide linked Fv. In some embodiments, the antibody is an IgG or an IgM. In some embodiments, the antibody is humanized. In some embodiments, the antibody is chimeric.

In some embodiments, the antibodies disclosed herein reduce level of soluble MICA protein. In some embodiments, the antibodies disclosed herein reduce level of soluble MICB protein. In some embodiments, the antibodies disclosed herein reduce level of both soluble MICA protein and soluble MICB protein. In some embodiments, the antibodies disclosed herein reduce shedding of soluble MICA protein. In some embodiments, the antibodies disclosed herein reduce shedding of soluble MICB protein. In some embodiments, the antibodies disclosed herein reduce shedding of both soluble MICA protein and soluble MICB protein. In some embodiments, the antibodies disclosed herein inhibit shedding of soluble MICA protein. In some embodiments, the antibodies disclosed herein inhibit shedding of soluble MICB protein. In some embodiments, the antibodies disclosed herein inhibit shedding of both soluble MICA protein and soluble MICB protein.

Any suitable route of administration is contemplated for use with the methods disclosed herein. In some embodiments, the antibody is administered by intravenous administration. In some embodiments, the antibody is administered by subcutaneous administration. In some embodiments, the antibody is administered locally. In some embodiments, the antibody is administered systemically (e.g., intravenously, intramuscularly, subcutaneously, intradermally, orally, intranasally, sublingually). In some embodiments, the antibody is formulated as a salve, lotion or emulsion. In some embodiments, the antibody is formulated as a solution. In some embodiments, the antibody is formulated for topical, oral, buccal, or nasal administration.

In some embodiments, the individual is monitored prior to administration of the antibody. Symptoms are identified and their severity is assessed. An antibody as described herein is administered alone or in combination with additional treatments, singly or multiply over time as discussed herein or known to one of skill in the art. In some embodiments, the individual is monitored such that the efficacy of the treatment regimen is determined. In some embodiments, a treatment regimen is modified in response to preliminary treatment outcomes, such that treatment dose or frequency or dose and frequency is altered so as to attain a desired level of subject response in light of symptom alleviation, side effect reduction, or a combination of symptom alleviation and side effect reduction.

Therapeutically effective amounts or dosages are contemplated to include dosages of about 0.01 mg/kg to about 20 mg/kg, about for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4 mg/kg, about 4.1 mg/kg, about 4.2 mg/kg, about 4.3 mg/kg, about 4.4 mg/kg, about 4.5 mg/kg, about 4.6 mg/kg, about 4.7 mg/kg, about 4.8 mg/kg, about 4.9 mg/kg, about 5 mg/kg, about 5.1 mg/kg, about 5.2 mg/kg, about 5.3 mg/kg, about 5.4 mg/kg, about 5.5 mg/kg, about 5.6 mg/kg, about 5.7 mg/kg, about 5.8 mg/kg, about 5.9 mg/kg, about 6 mg/kg, about 6.1 mg/kg, about 6.2 mg/kg, about 6.3 mg/kg, about 6.4 mg/kg, about 6.5 mg/kg, about 6.6 mg/kg, about 6.7 mg/kg, about 6.8 mg/kg, about 6.9 mg/kg, about 7 mg/kg, about 7.1 mg/kg, about 7.2 mg/kg, about 7.3 mg/kg, about 7.4 mg/kg, about 7.5 mg/kg, about 7.6 mg/kg, about 7.7 mg/kg, about 7.8 mg/kg, about 7.9 mg/kg, about 8 mg/kg, about 8.1 mg/kg, about 8.2 mg/kg, about 8.3 mg/kg, about 8.4 mg/kg, about 8.5 mg/kg, about 8.6 mg/kg, about 8.7 mg/kg, about 8.8 mg/kg, about 8.9 mg/kg, about 9 mg/kg, about 9.1 mg/kg, about 9.2 mg/kg, about 9.3 mg/kg, about 9.4 mg/kg, about 9.5 mg/kg, about 9.6 mg/kg, about 9.7 mg/kg, about 9.8 mg/kg, about 9.9 mg/kg, about 10 mg/kg, about 10.1 mg/kg, about 10.2 mg/kg, about 10.3 mg/kg, about 10.4 mg/kg, about 10.5 mg/kg, about 10.6 mg/kg, about 10.7 mg/kg, about 10.8 mg/kg, about 10.9 mg/kg, about 11 mg/kg, about 11.1 mg/kg, about 11.2 mg/kg, about 11.3 mg/kg, about 11.4 mg/kg, about 11.5 mg/kg, about 11.6 mg/kg, about 11.7 mg/kg, about 11.8 mg/kg, about 11.9 mg/kg, about 12 mg/kg, about 12.1 mg/kg, about 12.2 mg/kg, about 12.3 mg/kg, about 12.4 mg/kg, about 12.5 mg/kg, about 12.6 mg/kg, about 12.7 mg/kg, about 12.8 mg/kg, about 12.9 mg/kg, about 13 mg/kg, about 13.1 mg/kg, about 13.2 mg/kg, about 13.3 mg/kg, about 13.4 mg/kg, about 13.5 mg/kg, about 13.6 mg/kg, about 13.7 mg/kg, about 13.8 mg/kg, about 13.9 mg/kg, about 14 mg/kg, about 14.1 mg/kg, about 14.2 mg/kg, about 14.3 mg/kg, about 14.4 mg/kg, about 14.5 mg/kg, about 14.6 mg/kg, about 14.7 mg/kg, about 14.8 mg/kg, about 14.9 mg/kg, about 15 mg/kg, about 15.1 mg/kg, about 15.2 mg/kg, about 15.3 mg/kg, about 15.4 mg/kg, about 15.5 mg/kg, about 15.6 mg/kg, about 15.7 mg/kg, about 15.8 mg/kg, about 15.9 mg/kg, about 16 mg/kg, about 16.1 mg/kg, about 16.2 mg/kg, about 16.3 mg/kg, about 16.4 mg/kg, about 16.5 mg/kg, about 16.6 mg/kg, about 16.7 mg/kg, about 16.8 mg/kg, about 16.9 mg/kg, about 17 mg/kg, about 17.1 mg/kg, about 17.2 mg/kg, about 17.3 mg/kg, about 17.4 mg/kg, about 17.5 mg/kg, about 17.6 mg/kg, about 17.7 mg/kg, about 17.8 mg/kg, about 17.9 mg/kg, about 18 mg/kg, about 18.1 mg/kg, about 18.2 mg/kg, about 18.3 mg/kg, about 18.4 mg/kg, about 18.5 mg/kg, about 18.6 mg/kg, about 18.7 mg/kg, about 18.8 mg/kg, about 18.9 mg/kg, about 19 mg/kg, about 19.1 mg/kg, about 19.2 mg/kg, about 19.3 mg/kg, about 19.4 mg/kg, about 19.5 mg/kg, about 19.6 mg/kg, about 19.7 mg/kg, about 19.8 mg/kg, about 19.9 mg/kg, about or 20 mg/kg. Therapeutically effective amounts or dosages, in some cases, are contemplated to include dosages of about 0.1 mg/kg to about 2.0 mg/kg.

Methods of treatment herein comprise one or more administrations of anti-MICAS antibodies in doses disclosed herein. In some embodiments, methods comprise one administration of anti-MICA/B antibodies. In some embodiments, methods comprise two administrations of anti-MICA/B antibodies. In some embodiments, methods comprise three administrations of anti-MICA/B antibodies. In some embodiments, methods comprise four administrations of anti-MICA/B antibodies. In some embodiments, methods comprise five administrations of anti-MICA/B antibodies. In some embodiments, methods comprise six administrations of anti-MICAS antibodies. In some embodiments, one or more administrations of anti-MICA/B antibodies are administered daily. In some embodiments, one or more administrations of anti-MICA/B antibodies are administered weekly. In some embodiments, one or more administrations of anti-MICA/B antibodies are administered biweekly. In some embodiments, one or more administrations of anti-MICA/B antibodies are administered monthly. In some embodiments, one or more administrations of anti-MICA/B antibodies are administered every three months. In some embodiments, one or more administrations of anti-MICA/B antibodies are administered every six months. In some embodiments, one or more administrations of anti-MICA/B antibodies are administered yearly.

In some embodiments, the methods of treatment disclosed herein, is a monotherapy. In some embodiments, the methods of treatment disclosed herein, is a combination therapy. In some embodiments, combination therapy comprises administrations of anti-MICA/B antibodies in combination with another therapeutic agent. In some embodiments, the therapeutic agent comprises a chemotherapeutic agent. In some embodiments, the chemotherapeutic agent include, but is not limited to, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, *vinca* alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, kinase inhibitors and immune checkpoint inhibitors. In some embodiments, the anti-MICA/B antibodies disclosed herein are administered in combination with a therapeutic agent that induces an immune response. In some embodiments, the anti-MICA/B antibodies disclosed herein are administered in combination with a therapeutic agent that inhibits downregulation of an immune response. In some embodiments, inducing an immune response comprises activation or upregulating activity of NK cells. In some embodiments, inducing an immune response comprises activation or upregulating activity of T cells. In some embodiments, the immune check point inhibitor target comprises PD-1. In some embodiments, the immune check point inhibitor target comprises PD-L1. In some embodiments, the immune checkpoint inhibitor comprises Pembrolizumab, Nivolumab, Cemiplimab, AMP-224, AMP-514, PDR001, Atezolizumab, Avelumab, Durvalumab, BMS-936559, and CK-301.

Pharmaceutical Compositions

Also disclosed herein are pharmaceutical compositions comprising anti-MICA/B antibodies disclosed herein and a pharmaceutically acceptable carrier or excipient.

In some embodiments, excipients for use with the compositions disclosed herein include maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In some embodiments, the compositions further comprise an additional therapeutic agent. In some embodiments, the therapeutic agent is a chemotherapeutic agent. The chemotherapeutic agents can include, among others, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, vinca alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors.

In some embodiments, the antibody and the therapeutic agent are in the same formulation. In some embodiments, the antibody and the therapeutic agent are in different formulation. In some embodiments, antibody described herein is used prior to the administration of the other therapeutic agent. In some embodiments, antibody described herein is used concurrently with the administration of the other therapeutic agent. In some embodiments, antibody described herein is used subsequent to the administration of the other therapeutic agent.

Pharmaceutical formulations, in some embodiments, are made to be compatible with a particular local, regional or systemic administration or delivery route. Thus, pharmaceutical formulations include carriers, diluents, or excipients suitable for administration by particular routes. Specific non-limiting examples of routes of administration for compositions herein are parenteral, e.g., intravenous, intra-arterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

In some embodiments, solutions or suspensions used for parenteral application a particular local, regional or systemic administration or delivery route. Thus, pharmaceutical formulations include carriers, diluents, or excipients suitable for administration by particular routes. Specific non-limiting examples of routes of administration for compositions herein are parenteral, e.g., intravenous, intra-arterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

In some embodiments, solutions or suspensions used for parenteral application include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. In some embodiments, pH is adjusted with acids or bases, such as hydrochloric acid or sodium hydroxide. Pharmaceutical formulations for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In some embodiments, the carrier is a solvent or dispersion medium containing, for example, water, ethanol, polyol (for example, glycerol, propylene glycol, and liquid polyetheylene glycol, and the like), or suitable mixtures thereof. Fluidity is maintained, in some embodiments, for example, by the use of a coating such as lecithin, by the maintenance of the required particle size in the case of dispersion, and by the use of surfactants. Antibacterial and antifungal agents include, for example, parabens, chlorobutanol, phenol, ascorbic acid, and thimerosal. Isotonic agents, for example, sugars; polyalcohols such as mannitol or sorbitol; or sodium chloride, in some embodiments, are included in the composition. In some cases, also included is an agent which delays absorption, in some embodiments, for example, aluminum monostearate or gelatin prolongs absorption of injectable compositions.

In some embodiments, sterile injectable formulations are prepared by incorporating the active composition in the required amount in an appropriate solvent with one or a combination of above ingredients. Generally, dispersions are prepared by incorporating the active composition into a sterile vehicle containing a basic dispersion medium and any other ingredient. In the case of sterile powders for the preparation of sterile injectable solutions, methods of preparation include, for example, vacuum drying and freeze-drying which yields a powder of the active ingredient plus any additional desired ingredient from a previously prepared solution thereof.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. In some embodiments, transmucosal administration is accomplished through the use of nasal sprays, inhalation devices (e.g., aspirators) or suppositories. For transdermal administration, the active compounds are formulated into ointments, salves, gels, creams or patches.

In some embodiments, the pharmaceutical formulations are prepared with carriers that protect against rapid elimination from the body, such as a controlled release formulation or a time delay material such as glyceryl monostearate or glyceryl stearate. The formulations, in some embodiments, are also delivered using articles of manufacture such as implants and microencapsulated delivery systems to achieve local, regional or systemic delivery or controlled or sustained release.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Antibody Binding Kinetics Measurement

Affinity kinetics was determined on a ForteBio Octet Red96 analyzer. Briefly, anti-MICA/B mAb (30 µg/ml) was captured on Dip and Read™ Anti-mouse IgG Fc Capture (AMC) Biosensors (ForteBio) at room temperature in an assay buffer of PBS+ 0.1% BSA+ 0.02% Tween– 20 (pH 7.2). Sensors ere washed in assay buffer and then incubated with purified 6×His-MICA*08 or 6×His-MICA*04 proteins (100 nM), in 2-fold dilution series for 5 minutes in assay buffer to determine association kinetics of the antibody with the protein antigen. Sensors were then incubated in assay buffer for 10 minutes to determine dissociation kinetics. The resulting kinetics parameters were calculated with ForteBio analysis suite 8.0 using a 1:1 model. Results for these assays are shown in Table 2.

TABLE 2

Kinetic measurements of anti-MICA/B antibodies to MICA antigen by BioLayer Interferometry.

| Antibody | KD (M) | kon (1/Ms) | kdis(1/s) |
|---|---|---|---|
| 3F9.E4 | 1.18E−09 | 3.83E+05 | 4.21E−04 |
| 16F10.C12 | 6.45E−09 | 9.33E+04 | 5.48E−04 |

Example 2. Antibody Binding to MICA/B Alleles

Figure 1B:
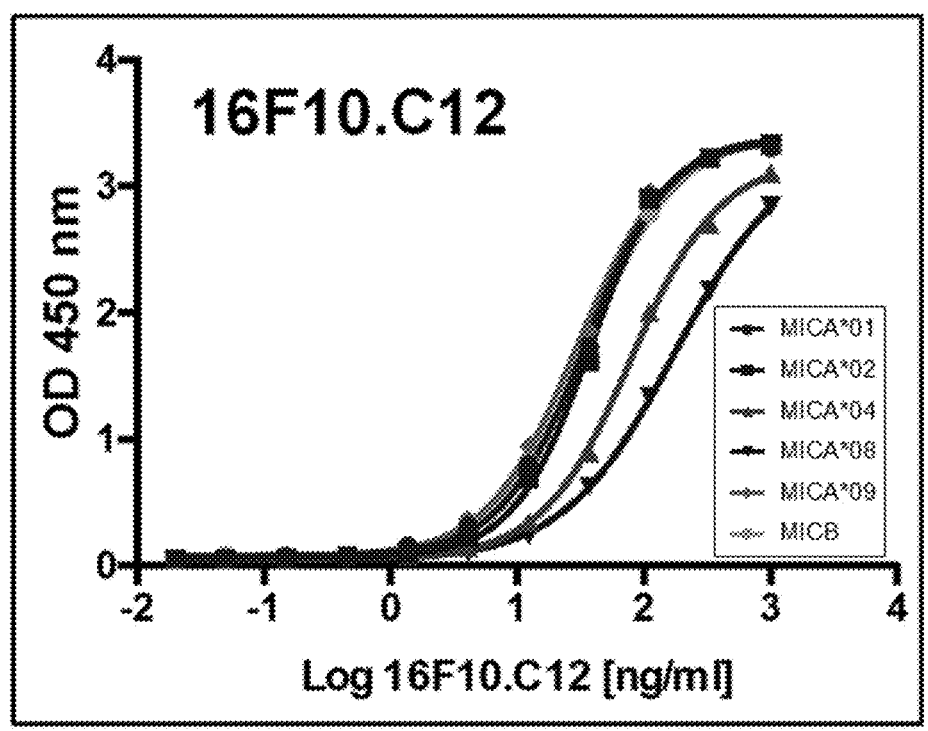

Recombinant MICA*01, MICA*02, MICA*04, MICA*08, MICA*09, and MICE proteins were diluted to 1 µg/ml in 50 mM sodium carbonate buffer, pH 9.6, and coated onto high binding 96-well microplates (Corning #9018), 100 ng in 100 ul per well. The following morning, coated ELISA plates were washed three times with TBS-Tween-20, pH 7.4 and then blocked in SuperBlock T20 Blocking Buffer (Pierce #37536). After blocking, ELISA plates were washed once with TBS-T and incubated with serially diluted anti-MICA antibody (0-1 µg/ml) for approximately two hours at room temperature. Following the incubation, ELISA plates were washed three times with TBS-T and then incubated with Goat anti-Mouse IgG (H+L)-HRP conjugate (ThermoFisher Scientific #626520) for 45 minutes at room temperature with shaking (~400 rpm). After the incubation, ELISA plates were washed three times with TBS-T and incubated with Super Sensitive Liquid Substrate TMB (Sigma #T4444), 100 ul per well, until color development was sufficient. The reaction was stopped with IN sulfuric acid, 100 ul per well. Optical density (OD) values were measured at 450 nm using a microplate reader. The results of this assay are shown in FIG. 1A-FIG. 1B.

Example 3. Antibody Binding to Cell Surface MICA

Figure 2:
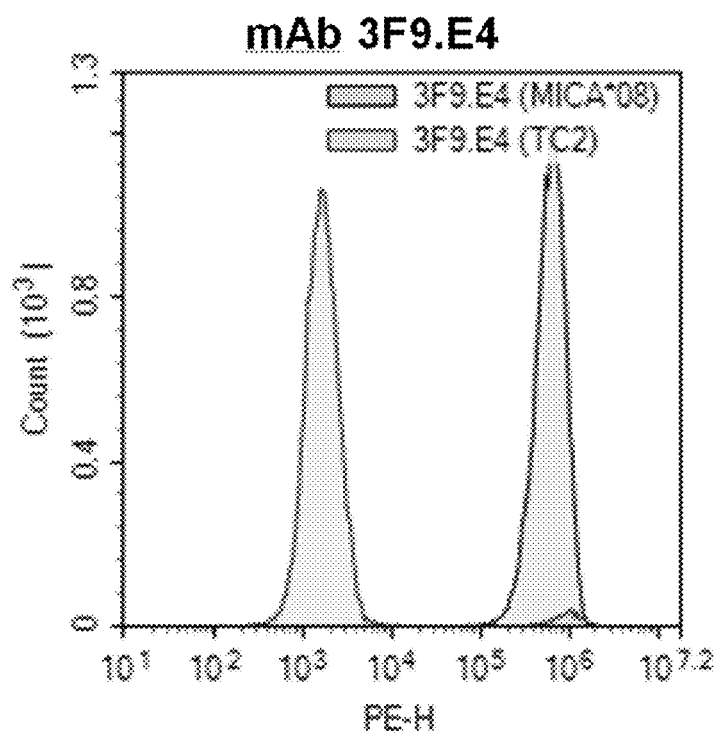
FIG. 2 exemplifies antibody 3F9.E4 binds to the cell surface MICA, evaluated by staining of TRAMP C2 cells transfected with MICA*08 in comparison to parental TC2 cells.

Mouse prostate adenocarcinoma TRAMP-C2 cells (TC2) (ATCC, Manassas, VA) were used to generate a stable cell line expressing MICA*08 allele (TC2-MICA-08). Binding of anti-MICA antibody to TC2-MICA-08 was analyzed by flow cytometry. Briefly, cells were first stained with LIVE/DEAD Near IR Stain (Thermo) for 30 min at 4° C., and then washed once by centrifugation with PACS Buffer (1 mM EDTA, 25 mM HEPES, 2% PBS in 1×PBS). About 2-3×10⁵ TC2-MICA-08 cells were incubated with 100 µl of PACS Buffer containing 500 ng anti-MICA antibody at 4° C. for 30 min, followed by incubation with 100 µl 2 µg/ml PE conjugated goat-anti-mouse IgG (Biolegend, San Diego, CA) secondary Ab at 4° C. for 30 min. Cells were then washed once and cell pellet resuspended with PACS Buffer for PACS analysis gated on live cells. Significantly higher PE fluorescence signal was observed with TC2-MICA-08 cells compared to parental TC2 cells indicated binding of anti-MICA mAb to surface expressed MICA. Result for this assay is shown in FIG. 2.

Example 4. Antibody Inhibits MICA Shedding from PLC/PRF/5 Cells

Figure 3:
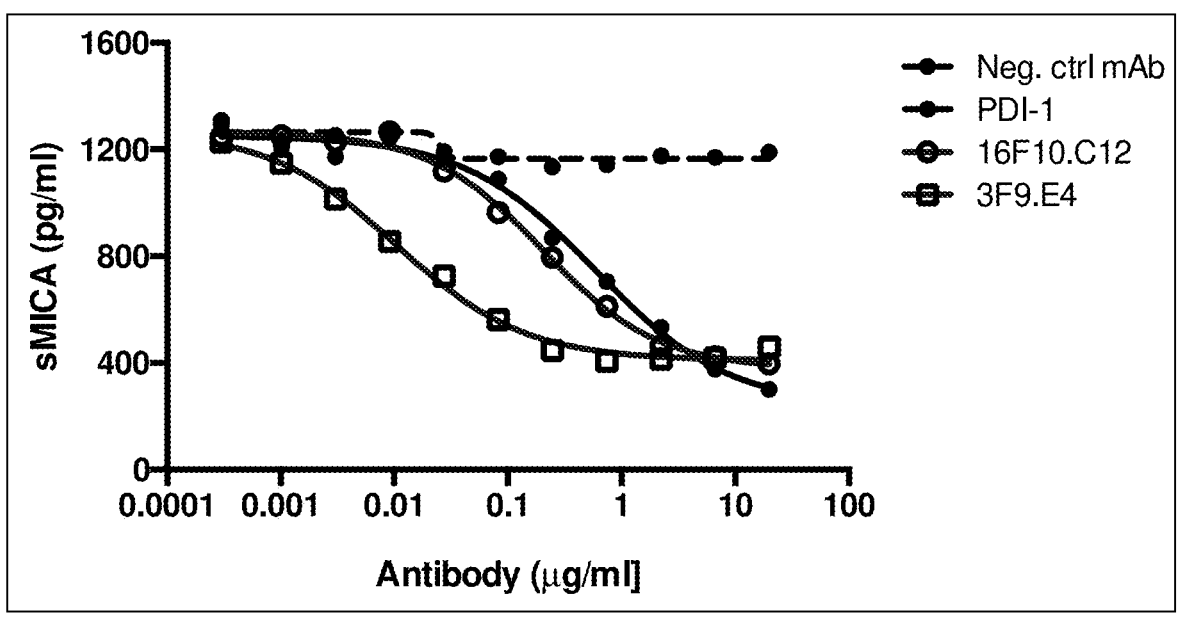
FIG. 3 exemplifies antibodies 3F9.E4 and 16F10.C12 inhibit MICA shedding from PLC/PRF/5 cells.

4×10⁴ PLC/PRP/5 cells (Hepatocellular Carcinoma) (ATCC, Manassas, VA) were plated in 96-well plate and incubated at 37° C. overnight. Cells were then treated with 100 µl Complete Media (MEM+10% PBS, Thermo, Grand Island, NY) containing anti-MICA antibody that binds to MICA α3 domain and negative control antibodies, respectively, and incubated at 37° C. for another day. Cell supernatants containing shed MICA were used to determine the level of soluble MICA by ELISA. Briefly, 96-well plate was coated with 100 µl 2 µg/ml anti-human MICA/B (clone BAMO1, MBL, Japan) overnight at 4° C. Plate was blocked and then incubated with cell supernatants and MICA standards for 2 hours. After incubation, plates were washed and followed by 1 hour incubation with 1 µg/ml proprietary anti-human MICA/MICB mAb, clone 10E9 conjugated with biotin. Next, 100 µl HRP conjugated streptavidin (HRP-SA) (R&D Systems, Minneapolis, MN) was added to wells and incubated for 30 min. Samples were developed with TMB for 4 min, stopped with 1N sulfuric acid and detected with absorbance at 450 nm. Soluble MICA level was interpolated from standard curve. Result for this assay is shown in FIG. 3.

Figure 4A:
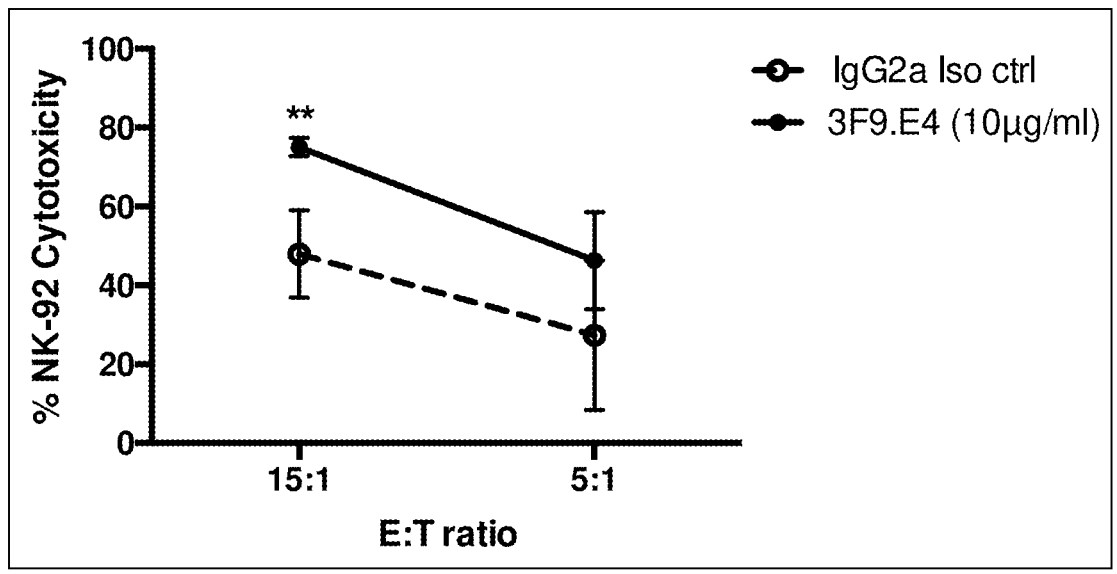
FIG. 4A-FIG. 4B exemplifies antibodies 3F9.E4 (FIG. 4A) and 16F10.C12 (FIG. 4B) enhance NK-92 cells mediated cytotoxicity of PLC/PRF/5 cells.
Figure 4B:
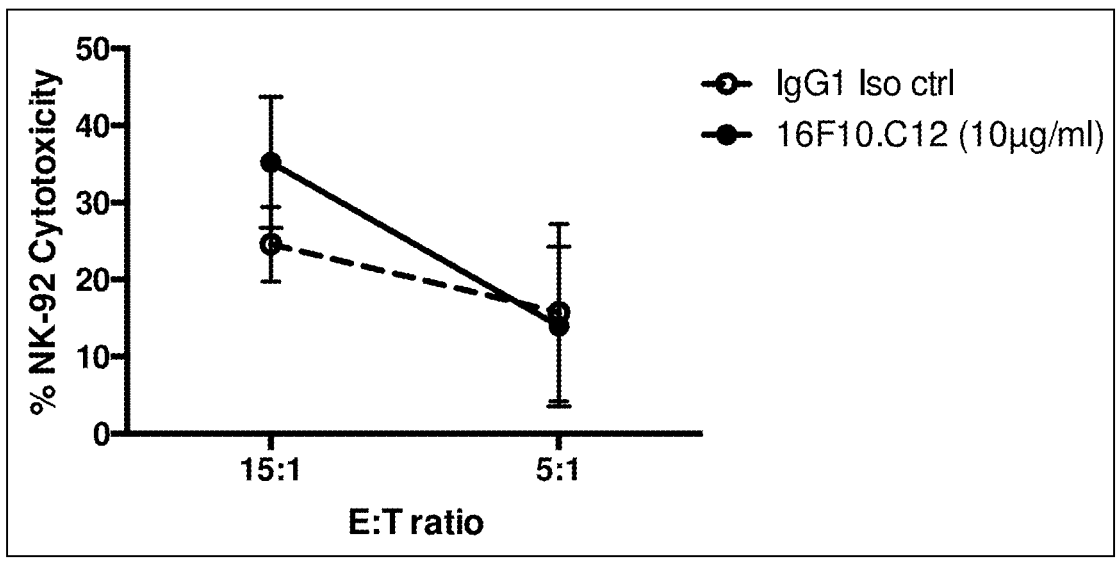

Example 5. Antibody Enhances NK-92 Cells Mediated Cytotoxicity to PLC/PRF/5 Cells PLC/PRP/5 (Target) cells were suspended in RPMI-1640 with 10% PBS, and plated into 96-well flat bottom plates (Costar) at 6000 cells/well. Cells were then incubated with anti-MICA antibody (10 µg/ml) that binds to MICA α3 domain for 24 hours before being labeled with calcein AM (1 μM) for 3 hours at 37° C., 5% CO2. Wells were washed, and NK-92 cells (Effector) suspended in RPMI-1640 with 10% PBS were then added to wells at various Effector-to-Target (E:T) ratios as indicated and co-cultured with target cells for 4 hours. At the end of the cultures, the supernatant was removed, replaced with PBS, and the calcein AM signal was measured using a VICTOR Multilabel plate reader (Perkin Elmer). An isotype matched nonreactive immunoglobulin (R&D) antibody was used as a control. Results for this assay are shown in FIG. 4A-FIG. 4B.

Figure 5:
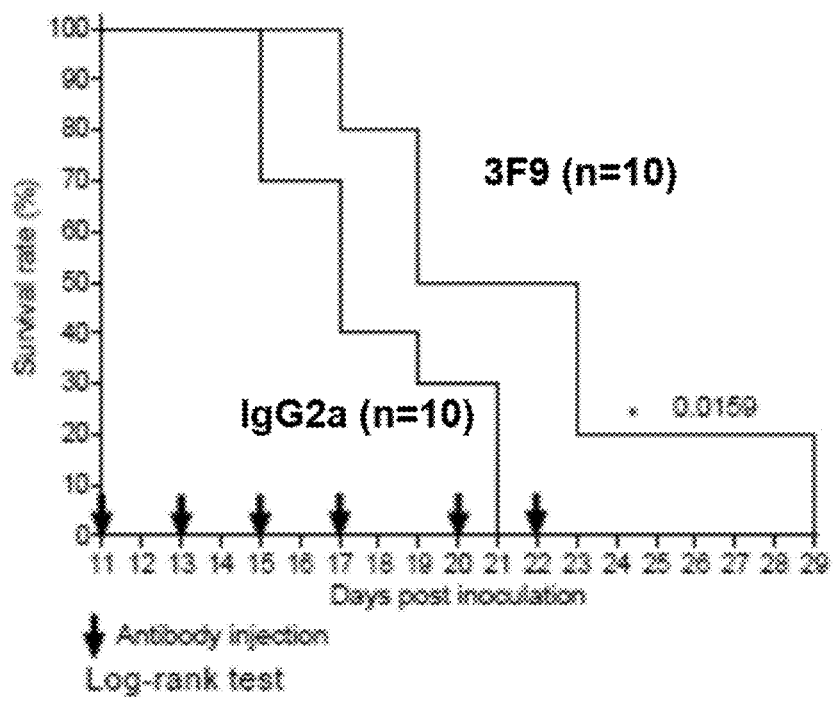
FIG. 5 exemplifies antitumor activity of antibody 3F9 against B16/MICA transfectants relative to isotype control (IC).

Example 6. Efficacy of 3F9.E4 in Tumor Therapy In Vivo (Survival) and NKG2S Expression by Tumor-Infiltrating Lymphocytes in Tumor-Bearing Mice MICA transgenic mice (MICAgen) were inoculated with $10^4$ B16F10-MICA*01 cells (B16 transfectant) and, upon day 11, when tumors reached the desired threshold size, mice were treated with 3F9 or isotype control (arrows indicate days of injection) (Log-rank test). Results are shown in FIG. 5.

Figure 6A:
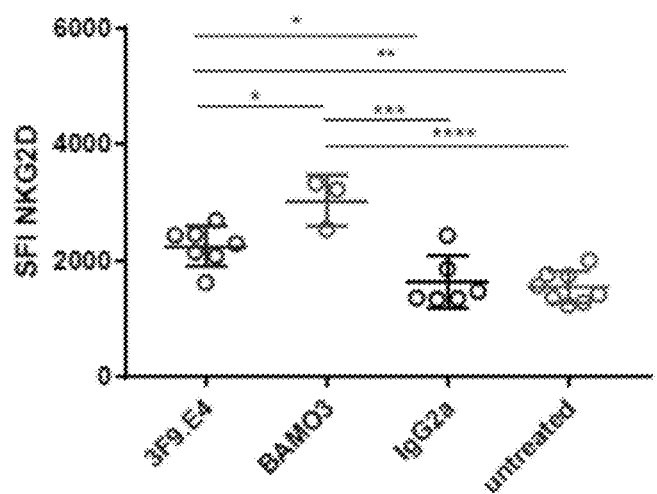
FIG. 6A-FIG. 6C exemplify higher percentage of NKG2D positive NK cells (FIG. 6A), CD8+ T cells (FIG. 6B) and gamma delta T cells (FIG. 6C) are observed in tumor infiltrates (TILs) in 3F9.E4 antibody treated tumors compared to isotype control.
Figure 6B:
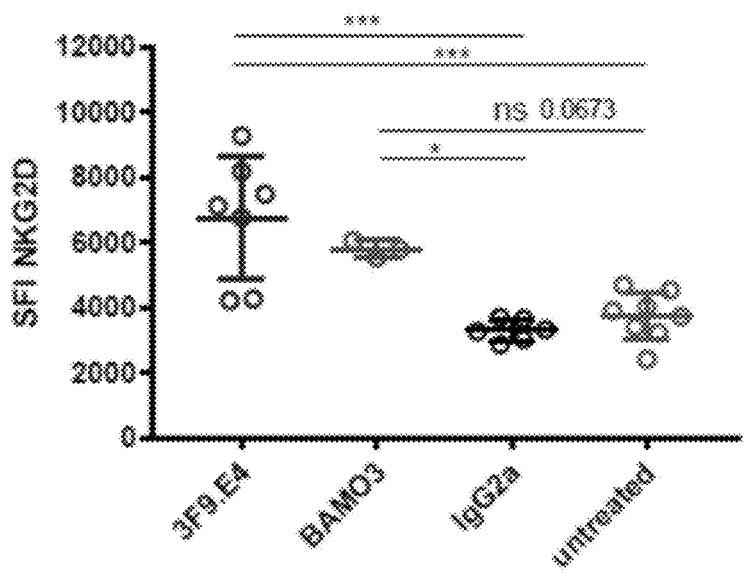
Figure 6C:
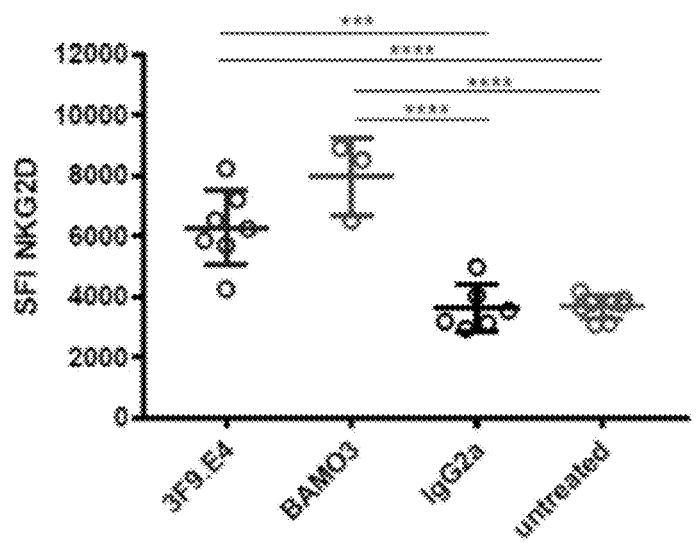

Mice were sacrificed when reaching a high tumor load and tumor-infiltrating lymphocytes analyzed for NKG2D expression (SFI) by NK cells, CD8 αβ T cells, and γδ T cells. NKG2D expression strength (SFI) of NKG2D-expressing cells are shown in FIG. 6A-FIG. 6C. Each symbol represents analyses of an individual mouse. (One-way ANOVA+Tukey's multiple comparisons test).

Figure 7A:
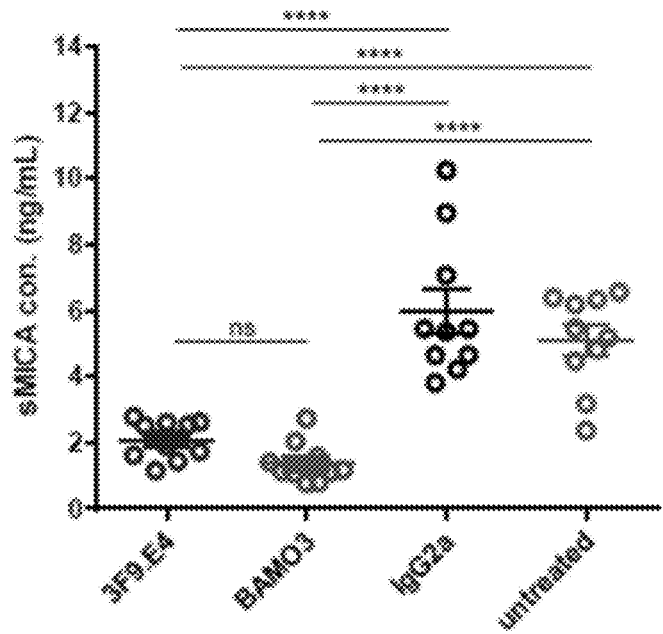
FIG. 7A-FIG. 7B exemplify treatment with 3F9.E4 antibody in B16/MICA in MICA transgenic animals reduces levels of soluble MICA (FIG. 7A) and surface MICA in tumors (FIG. 7B).
Figure 7B:
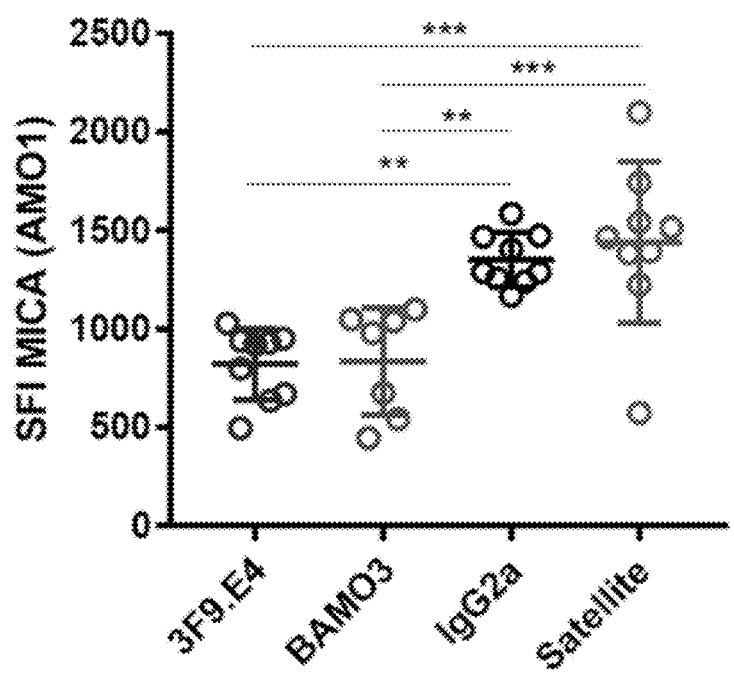

Example 7. MICA Expression by B16 Transfectant Tumors Ex Vivo and Detection of Soluble MICA in Sera of Tumor-Bearing Mice MICA transgenic mice (MICAgen) were inoculated with $10^4$ B16F10-MICA*01 cells (B16 transfectant) and, upon day 11, when tumors reached the desired threshold size, mice were treated with 3F9.E4 or BAMO3 or isotype control. Mice were sacrificed when reaching a high tumor load and isolated single tumor cells analyzed for MICA expression with mAb AMO1 staining (One-way ANOVA+ Tukey's multiple comparisons test). AMO1 binds to the ala2-domain of MICA (i-BAMO3 and 3F9). Each symbol represents analysis of an individual mouse. Results are shown in FIG. 7B. Sera was also analyzed for sMICA using AMO1/BAMO1 sandwich ELISA. Each symbol represents an individual mouse (Unpaired t-test). Results are shown in FIG. 7A.

Example 8. Epitope Binning

Figure 8A:
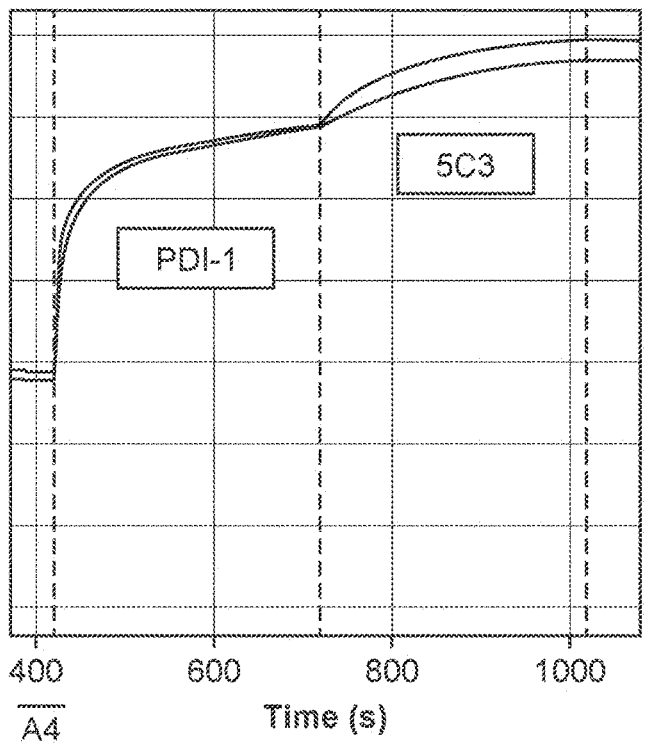
FIG. 8A-FIG. 8C exemplify competition binding assay to illustrate that all antibodies bind to a "structural" epitope and antibody 3F9.E4 competitively binds antibody PDI-1 (FIG. 8B) and antibody 16F10 binds a slightly different epitope than PDI-1 and 3F9, but in close proximity (FIG. 8C).
Figure 8B:
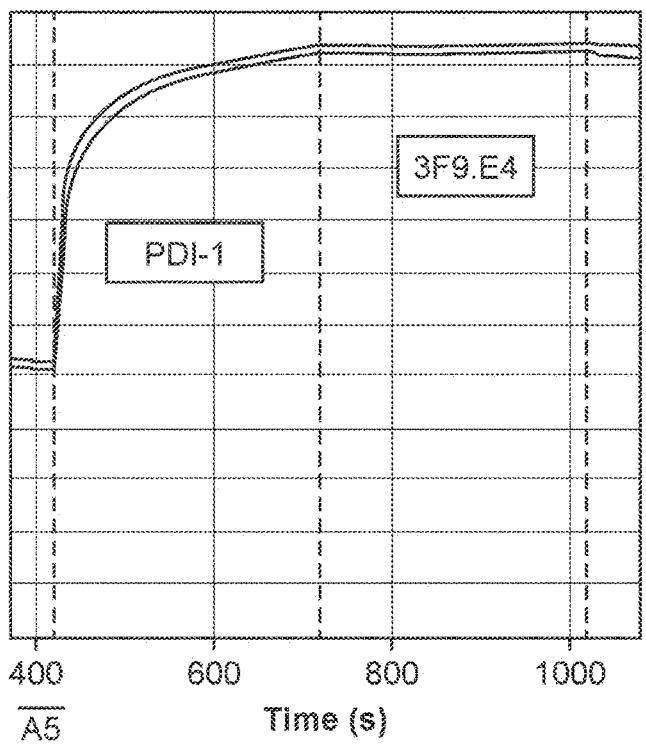
Figure 8C:
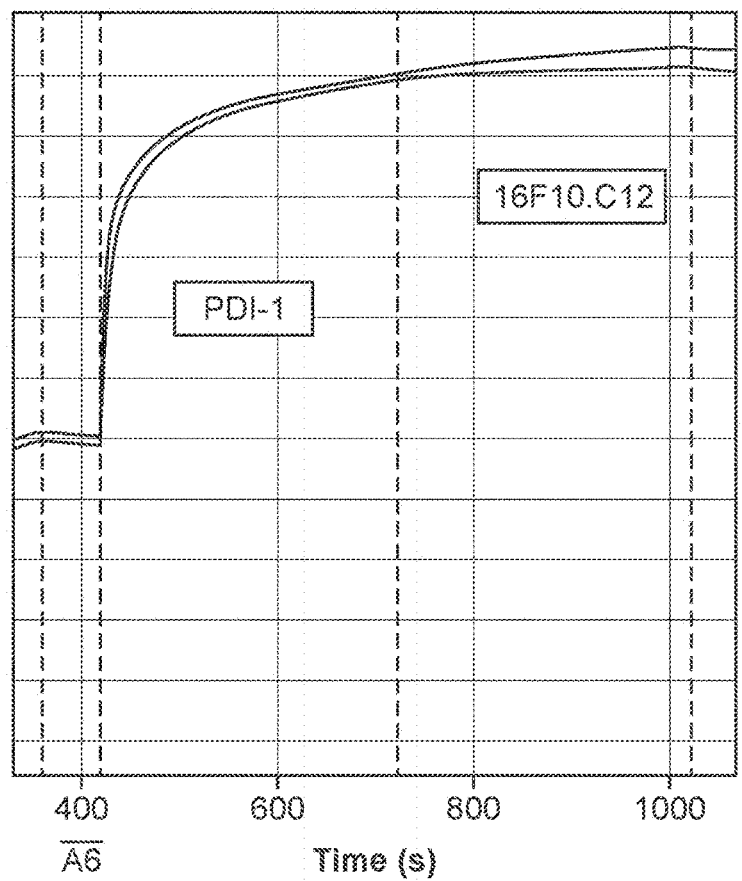

MICA *04-His protein (30 μg/ml) was immobilized onto Ni-NTA (FortrBio, #18-5101) biosensor tips for a biolayer interferometry instrument (Octet Red, ForteBio) for 300 s. The baseline signal was measured again for 60 s before biosensor tips were immersed into wells containing 1 mM or 0.5 mM of primary antibody for 300 s. Following this process, biosensors were immersed into wells containing 100 nM or 50 nM of a second mAb for 300 s. Percent binding of a second mAbs in the presence of the first mAb was determined by comparing the maximal signal of the second mAb after the first mAb was added to the maximum signal of the second mAb alone. mAbs were considered noncompeting if maximum binding of the second mAb was ≥66% of its uncompeted binding. A level between 33% and 66% of its uncompeted binding was considered intermediate competition, and ≤33% was considered competing. Results for this assay are shown in FIG. 8A-FIG. 8C.

While preferred embodiments of the present invention have been shown and describe herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. A monoclonal antibody or an antigen-binding fragment thereof, comprising, light chain complementarity determining regions (LCDR) 1-3 and heavy chain complementarity determining regions (HCDR) 1-3 as follows:
   a. LCDR1 is SEQ ID NO: 1, LCDR2 is SEQ ID NO: 2, LCDR3 is SEQ ID NO: 3, HCDR1 is SEQ ID NO: 4, HCDR2 is SEQ ID NO: 5, and HCDR3 is SEQ ID NO: 6; or
   b. LCDR1 is SEQ ID NO: 9, LCDR2 is SEQ ID NO: 10, LCDR3 is SEQ ID NO: 11, HCDR1 is SEQ ID NO: 12, HCDR2 is SEQ ID NO: 13, and HCDR3 is SEQ ID NO: 14; or
   c. LCDR1 is SEQ ID NO: 17, LCDR2 is SEQ ID NO: 2, LCDR3 is SEQ ID NO: 3, HCDR1 is SEQ ID NO: 4, HCDR2 is SEQ ID NO: 18, and HCDR3 is SEQ ID NO: 6.

2. A monoclonal antibody or antigen-binding fragment thereof comprising a light chain variable domain (VL) having an amino acid sequence comprising 100% sequence identity to SEQ ID NO: 19 and a heavy chain variable domain (VH) having an amino acid sequence comprising 100% sequence identity to SEQ ID NO: 20.

3. The monoclonal antibody or antigen-binding fragment thereof of claim 1, wherein the monoclonal antibody or antigen-binding fragment thereof specifically binds to a MICA protein, a MICB protein, or both MICA and MICB protein.

4. The monoclonal antibody or antigen-binding fragment thereof of claim 3, wherein the MICA protein is membrane-bound MICA protein, soluble MICA protein, or both.

5. The monoclonal antibody or antigen-binding fragment thereof of claim 3, wherein the MICB protein is membrane-bound MICB protein, soluble MICB protein, or both.

6. The monoclonal antibody or antigen-binding fragment thereof of claim 1, wherein the monoclonal antibody or antigen-binding fragment thereof is selected from a whole immunoglobulin, an scFv, a Fab, a F(ab')2, or a disulfide linked Fv.

7. The monoclonal antibody or antigen-binding fragment thereof of claim 1, wherein the monoclonal antibody or antigen-binding fragment thereof is an IgG or IgM.

8. The monoclonal antibody or antigen-binding fragment thereof of claim 1, wherein the monoclonal antibody or antigen-binding fragment thereof is humanized or chimeric.

9. A pharmaceutical composition comprising: a monoclonal antibody or an antigen-binding fragment thereof according to claim 1; and a pharmaceutically acceptable carrier or excipient.

10. The monoclonal antibody or antigen-binding fragment thereof of claim 2, wherein the monoclonal antibody or antigen-binding fragment thereof specifically binds to a MICA protein, a MICB protein, or both MICA and MICB protein.

11. The monoclonal antibody or antigen-binding fragment thereof of claim 10, wherein the MICA protein is membrane-bound MICA protein, soluble MICA protein, or both.

12. The monoclonal antibody or antigen-binding fragment thereof of claim 10, wherein the MICB protein is membrane-bound MICB protein, soluble MICB protein, or both.

13. The monoclonal antibody or antigen-binding fragment thereof of claim 2, wherein the monoclonal antibody or antigen-binding fragment thereof is selected from a whole immunoglobulin, an scFv, a Fab, a F(ab')2, or a disulfide linked Fv.

14. The monoclonal antibody or antigen-binding fragment thereof of claim 2, wherein the monoclonal antibody or antigen-binding fragment thereof is an IgG or IgM.

15. The monoclonal antibody or antigen-binding fragment thereof of claim 2, wherein the monoclonal antibody or antigen-binding fragment thereof is humanized or chimeric.

16. A pharmaceutical composition comprising: a monoclonal antibody or an antigen-binding fragment thereof according to claim 2; and a pharmaceutically acceptable carrier or excipient.

* * * * *